(12) United States Patent
Folan et al.

(10) Patent No.: US 10,285,809 B2
(45) Date of Patent: May 14, 2019

(54) TAVI ANCHORING ASSIST DEVICE

(71) Applicants: BOSTON SCIENTIFIC SCIMED, INC.; Juan F. Granada, Saddle Rock, NJ (US)

(72) Inventors: Martyn G. Folan, Galway (IE); Juan F. Granada, Saddle River, NJ (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 61 days.

(21) Appl. No.: 15/060,258

(22) Filed: Mar. 3, 2016

(65) Prior Publication Data

US 2016/0256270 A1   Sep. 8, 2016

Related U.S. Application Data

(60) Provisional application No. 62/129,184, filed on Mar. 6, 2015, provisional application No. 62/204,090, filed on Aug. 12, 2015.

(51) Int. Cl.
*A61F 2/24*   (2006.01)

(52) U.S. Cl.
CPC ......... *A61F 2/2418* (2013.01); *A61F 2/2409* (2013.01); *A61F 2/2436* (2013.01);
(Continued)

(58) Field of Classification Search
CPC .... A61F 2/2418; A61F 2/2409; A61F 2/2436; A61F 2/2439
See application file for complete search history.

(56) References Cited

U.S. PATENT DOCUMENTS

| 15,192 A | 6/1856 | Peale |
|---|---|---|
| 2,682,057 A | 6/1954 | Lord |

(Continued)

FOREIGN PATENT DOCUMENTS

| CN | 1338951 A | 3/2002 |
|---|---|---|
| DE | 19532846 A1 | 3/1997 |

(Continued)

OTHER PUBLICATIONS

US 8,062,356 B2, 11/2011, Salahieh et al. (withdrawn)
(Continued)

*Primary Examiner* — Dinah Baria
(74) *Attorney, Agent, or Firm* — Seager, Tufte & Wickhem LLP.

(57) ABSTRACT

An implant system may include a delivery sheath having an actuator mechanism, an anchoring assistance device including an expandable scaffold including a mid-body section, a cusp interface section, and a crown end arrangement, and a replacement heart valve implant. The cusp interface section includes a plurality of loop portions arranged at radial intervals about the expandable scaffold. Each loop portion is circumferentially spaced apart from another loop portion by a region having a deployment ring, the region being configured to span a commissure of the aortic valve and extending distally a shorter distance from the distal end than the loop portions. An elongate deployment member is configured to releasably engage with the deployment rings to actuate the expandable scaffold from a delivery configuration to a deployed configuration. The replacement heart valve implant is configured to be at least partially disposed within the expandable scaffold in the deployed configuration.

15 Claims, 22 Drawing Sheets

(52) U.S. Cl.
CPC .... *A61F 2/2439* (2013.01); *A61F 2230/0054* (2013.01); *A61F 2250/0003* (2013.01); *A61F 2250/006* (2013.01); *A61F 2250/0037* (2013.01); *A61F 2250/0069* (2013.01)

(56) References Cited

U.S. PATENT DOCUMENTS

| | | |
|---|---|---|
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |
| 5,545,209 A | 8/1996 | Roberts et al. |

(56) References Cited

U.S. PATENT DOCUMENTS

| | | |
|---|---|---|
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Ladno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsuigita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B2 | 1/2003 | Pavcnik et al. |

(56) References Cited

U.S. PATENT DOCUMENTS

| | | |
|---|---|---|
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | Dubois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |
| 7,892,292 B2 | 2/2011 | Stack et al. |

(56) References Cited

U.S. PATENT DOCUMENTS

| | | |
|---|---|---|
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| RE45,130 E * | 9/2014 | Figulla ................. 623/1.15 |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |

(56) References Cited

U.S. PATENT DOCUMENTS

| | | |
|---|---|---|
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |

(56) References Cited

U.S. PATENT DOCUMENTS

| | | |
|---|---|---|
| 2009/0093877 A1 | 4/2009 | Keidar et al. |
| 2009/0171456 A1 | 7/2009 | Kveen et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0049313 A1 | 2/2010 | Alon et al. |
| 2010/0094399 A1 | 4/2010 | Dorn et al. |
| 2010/0121434 A1 | 5/2010 | Paul et al. |
| 2010/0168839 A1 | 7/2010 | Braido et al. |
| 2010/0191326 A1 | 7/2010 | Alkhatib |
| 2010/0219092 A1 | 9/2010 | Salahieh et al. |
| 2010/0280495 A1 | 11/2010 | Paul et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0197379 A1 | 8/2012 | Laske et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0123796 A1 | 5/2013 | Sutton et al. |
| 2013/0158656 A1 | 6/2013 | Sutton et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0236289 A1 | 8/2014 | Alkhatib |
| 2014/0243967 A1 | 8/2014 | Salahieh et al. |
| 2014/0249621 A1 | 9/2014 | Eidenschink |
| 2015/0032206 A1 | 1/2015 | Alkhatib |
| 2015/0265400 A1* | 9/2015 | Eidenschink ......... A61F 2/2427 623/2.18 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1078610 B1 | 8/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| FR | 2788217 A1 | 7/2000 |
| GB | 2056023 A | 3/1981 |
| GB | 2398245 A | 8/2004 |
| JP | 2010536527 A | 12/2010 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 0504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |

(56) References Cited

FOREIGN PATENT DOCUMENTS

| | | |
|---|---|---|
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 204066876 A1 | 8/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 5/2007 |
| WO | 2007058847 A2 | 5/2007 |
| WO | 2007092354 A2 | 8/2007 |
| WO | 2007097983 A2 | 8/2007 |
| WO | 2009014617 A1 | 1/2009 |
| WO | 2010042950 A2 | 4/2010 |
| WO | 2011101128 A1 | 8/2011 |
| WO | 2012116368 A2 | 8/2012 |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Andersen et al., "Transluminal implantation of artificial heart valves. Description of a new expandable aortic valve and initial results with implantation by catheter technique in closed chest pigs." Euro. Heart J., 13:704-708, 1992.
Atwood et al., "Insertion of Heart Valves by Catheterization." Project Supervised by Prof. S. Muftu of Northeastern University 2001-2002: 36-40.
Bodnar et al., "Replacement Cardiac Valves R Chapter 13: Extinct Cardiac Valve Prostheses." Pergamon Publishing Corporation. New York, 1991: 307-322.
Boudjemline et al. "Percutaneous Implantation of a Biological Valve in the Aorta to Treat Aortic Valve Insufficiency—A Sheep Study." Med Sci. Monit., vol. 8, No. 4: BR113-116, 2002.
Boudjemline et al., "Percutaneous Implantation of a Valve in the Descending Aorta in Lambs." Euro. Heart J., 23: 1045-1049, 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, 2004.
Boudjemline et al., "Percutaneous Valve Insertion: A New Approach?" J. of Thoracic and Cardio. Surg, 125(3): 741-743, 2003.
Boudjemline et al., "Steps Toward Percutaneous Aortic Valve Replacement." Circulation, 105: 775-778, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, 2004.
Cribier et al., "Percutaneous Transcatheter Implementation of an Aortic Valve Prosthesis for Calcific Aortic Stenosis: First Human Case Description." Circulation, 106: 3006-3008, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, 2002.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Hijazi, "Transcatheter Valve Replacement: A New Era of Percutaneous Cardiac Intervention Begins." J. of Am. College of Cardio., 43(6): 1088-1089, 2004.
Huber et al., "Do Valved Stents Compromise Coronary Flow?" European Journal of Cardio-thoracic Surgery, vol. 25: 754-759, 2004.
Knudsen et al., "Catheter-implanted prosthetic heart valves." Int'l J. of Art. Organs, 16(5): 253-262, 1993.
Kort et al., "Minimally Invasive Aortic Valve Replacement: Echocardiographic and Clinical Results." Am. Heart J., 142(3): 476-481, 2001.
Love et al., The Autogenous Tissue Heart Valve: Current Status. Journal of Cardiac Surgery, 6(4): 499-507, 1991.
Lutter et al., "Percutaneous Aortic Valve Replacement: An Experimental Study. I. Studies on Implantation." J. of Thoracic and Cardio. Surg., 123(4): 768-776, 2002.
Moulopoulos et al., "Catheter-Mounted Aortic Valves." Annals of Thoracic Surg., 11(5): 423-430, 1971.
Paniagua et al., "Percutaneous Heart Valve in the Chronic in Vitro Testing Model." Circulation, 106: e51-e52, 2002.
Paniagua et al., "Heart Watch." Texas Heart Institute. Spring, 2004. Edition: 8 pages.
Pavcnik et al., "Percutaneous Bioprosthetic Veno Valve: A Long-term Study in Sheep." J. of Vascular Surg., 35(3): 598-603, 2002.
Phillips et al., "A Temporary Catheter-Tip Aortic Valve: Hemodynamic Effects on Experimental Acute Aortic Insufficiency." Annals of Thoracic Surg., 21(2): 134-136, 1976.
Sochman et al., "Percutaneous Transcatheter Aortic Disc Valve Prosthesis Implantation: A Feasibility Study." Cardiovasc. Intervent. Radiol., 23: 384-388, 2000.
Stuart, "In Heart Valves, A Brave, New Non-Surgical World." Start-Up. 9-17, 2004.
Vahanian et al., "Percutaneous Approaches to Valvular Disease." Circulation, 109: 1572-1579, 2004.
Van Herwerden et al., "Percutaneous Valve Implantation: Back to the Future?" Euro. Heart J., 23(18): 1415-1416, 2002.
Zhou et al, "Self-expandable Valved Stent of Large Size: Off-Bypass Implantation in Pulmonary Position." Eur. J. Cardiothorac, 24: 212-216, 2003.
Examiner's First Report on AU Patent Application No. 2011202667, dated May 17, 2012.
"A Matter of Size." Treiennial Review of the National Nanotechnology Initiative, The National Academies Press, Washington DC, v-13, 2006, http://www.nap.edu/catalog/11752/a-matter-of-size-triennial-review-of-the-national-nanotechnology.
Atwood et al., "Insertion of Heart Valves by Catheterization." The Capstone Design Course Report. MIME 1501-1502. Technical Design Report. Northeastern University, pp. 1-93, Nov. 5, 2007.
Aug. 19, 2011, Supplemental Search Report from EP Patent Office, EP Application No. 04813777.2.
Aug. 19, 2011, Supplemental Search Report from EP Patent Office, EP Application No. 04815634.3.
Cunanan et al., "Tissue Characterization and Calcification Potential of Commerical Bioprosthetic Heart Valves." Ann. Thorac. Surg., S417-421, 2001.

(56) References Cited

OTHER PUBLICATIONS

Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report dated Aug. 10, 2011 for EP Application No. 06824992.9.
"Heart Valve Materials—Bovine (cow)." Equine & Porcine Pericardium, Maverick Biosciences Pty. Lt, http://maverickbio.com/biological-medical-device-materials.php?htm. 2009.
Helmus, "Mechanical and Bioprosthetic Heart Valves in Biomaterials for Artificial Organs." Woodhead Publishing Limited: 114-162, 2011.
Hourihan et al., "Transcatheter Umbrella Closure of Valvular and Paravalvular Leaks." JACC, Boston, Massachusetts, 20(6): 1371-1377, Nov. 15, 1992.
Laborde et al., "Percutaneous Implantation of the Corevalve Aortic Valve Prosthesis for Patients Presenting High Risk for Surgical Valve Replacement." EuroIntervention: 472-474, 2006.
Levy, "*Mycobacterium chelonei* Infection of Porcine Heart Valves." The New England Journal of Medicine, Washington DC, 297(12), Sep. 22, 1977.
Supplemental Search Report from EP Patent Office, EP Application No. 05758878.2, dated Oct. 24, 2011.
"Pericardial Heart Valves." Edwards Lifesciences, Cardiovascular Surgery FAQ, Nov. 14, 2010, http://www.edwards.com/products/cardiovascularsurgeryfaq.htm.
Southern Lights Biomaterials Homepage, Jan. 7, 2011, http://www.slv.co.nz/.
Stassano. "Mid-term Results of the Valve-on-Valve Technique for Bioprosthetic Failure." European Journal of Cardiothoracic Surgery: 453-457, 2000.
Topol. "Percutaneous Expandable Prosthetic Valves." Textbook of Interventional Cardiology, W.B. Saunders Company, 2: 1268-1276, 1994.
International Search Report and Written Opinion PCT/US2016/010881, dated Jun. 20, 2016.
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Bodnar et al., "Replacement Cardiac Valves R Chapter 13: Extinct Cardiac Valve Prostheses." Pergamon Publishing Corporation. New York, 307-322, 1991.
Boudjemline et al. "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Hijazi, "Transcatheter Valve Replacement: A New Era of Percutaneous Cardiac Intervention Begins." J. of Am. College of Cardio., 43(6): 1088-1089, Mar. 17, 2004.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Percutaneous Heart Valve in the Chronic in Vitro Testing Model." Circulation, 106: e51-e52, Sep. 17, 2002.
Paniagua et al., "Heart Watch." Texas Heart Institute. Edition: 8 pages, Spring, 2004.
Pavcnik et al., "Percutaneous Bioprosthetic Venous Valve: A Long-term Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Stuart, "In Heart Valves, A Brave, New Non-Surgical World." Start-Up. 9-17, Feb. 2004.
Stassano. "Mid-term Results of the Valve-on-Valve Technique for Bioprosthetic Failure." European Journal of Cardiothoracic Surgery: vol. 18, 453-457, Oct. 2000.
"A Matter of Size." Triennial Review of the National Nanotechnology Initiative, The National Academies Press, Washington DC, v-13, http://www.nap.edu/catalog/117521a-matter-of-size-triennial-review-of-the-national-nanotechnology, 2006.
Cunanan et al., "Tissue Characterization and Calcification Potential of Commercial Bioprosthetic Heart Valves." Ann. Thorac. Surg., S417-421, May 15, 2001.
Laborde et al., "Percutaneous Implantation of the Corevalve Aortic Valve Prosthesis for Patients Presenting High Risk for Surgical Valve Replacement." EuroIntervention: 472-474, Feb. 2006.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.

* cited by examiner

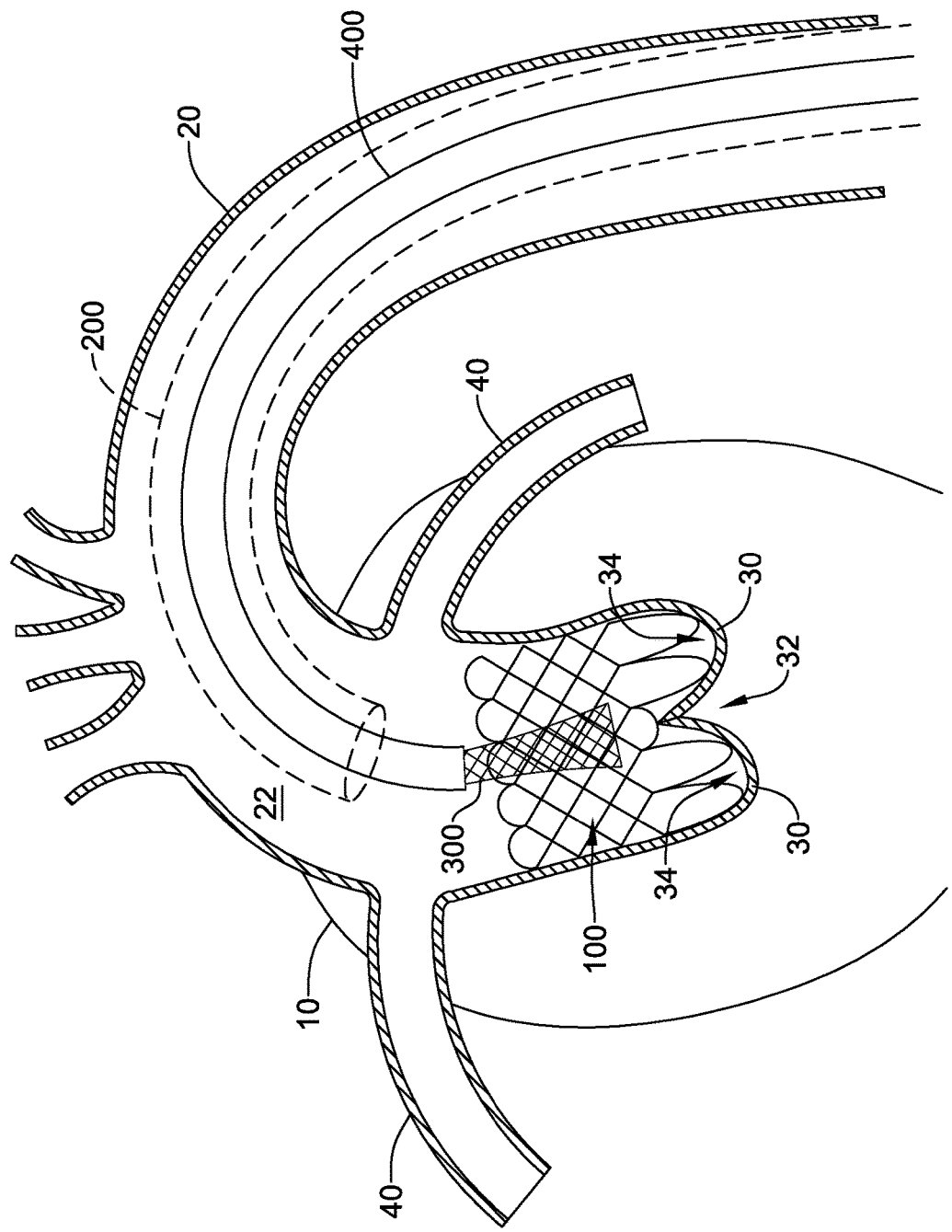

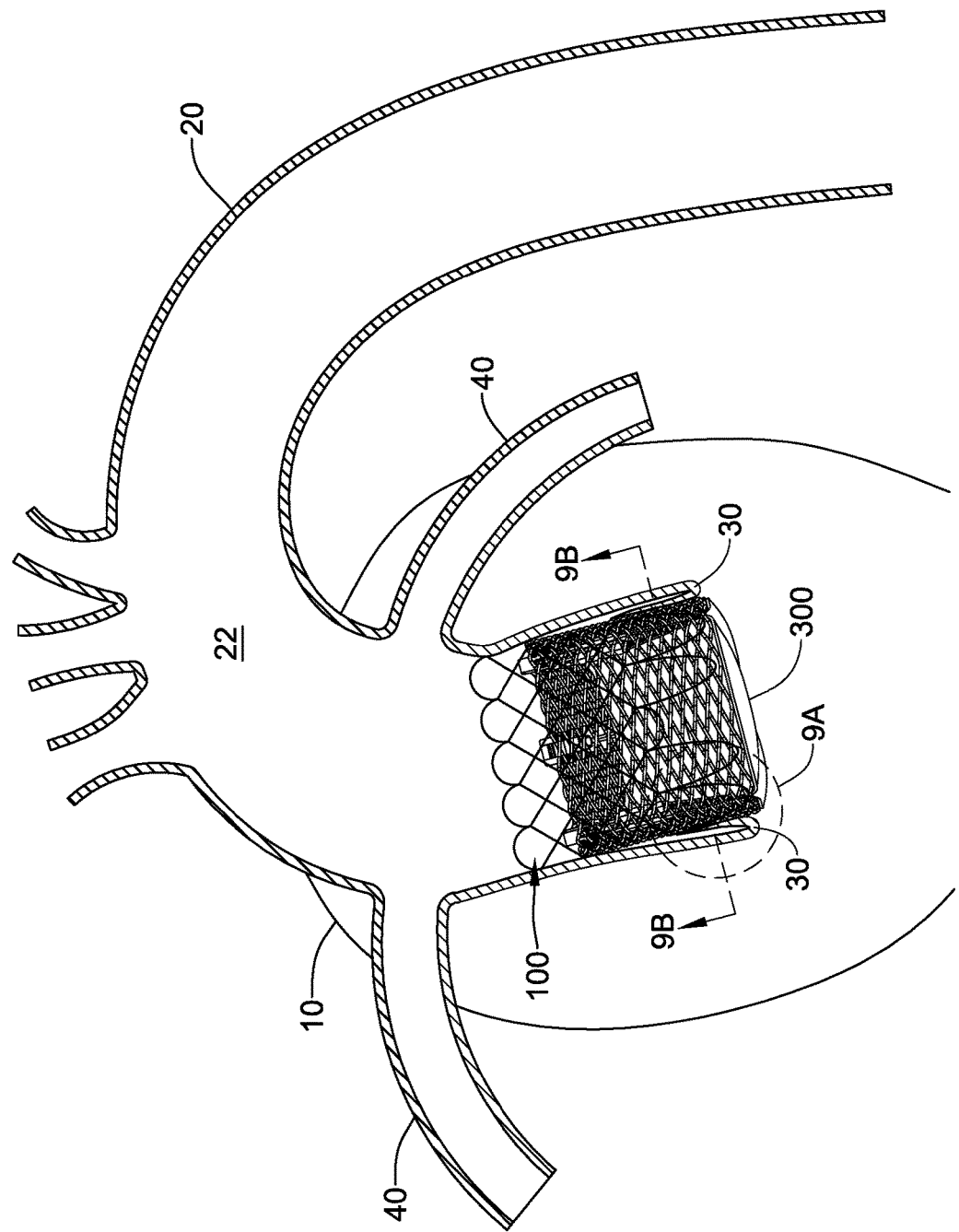

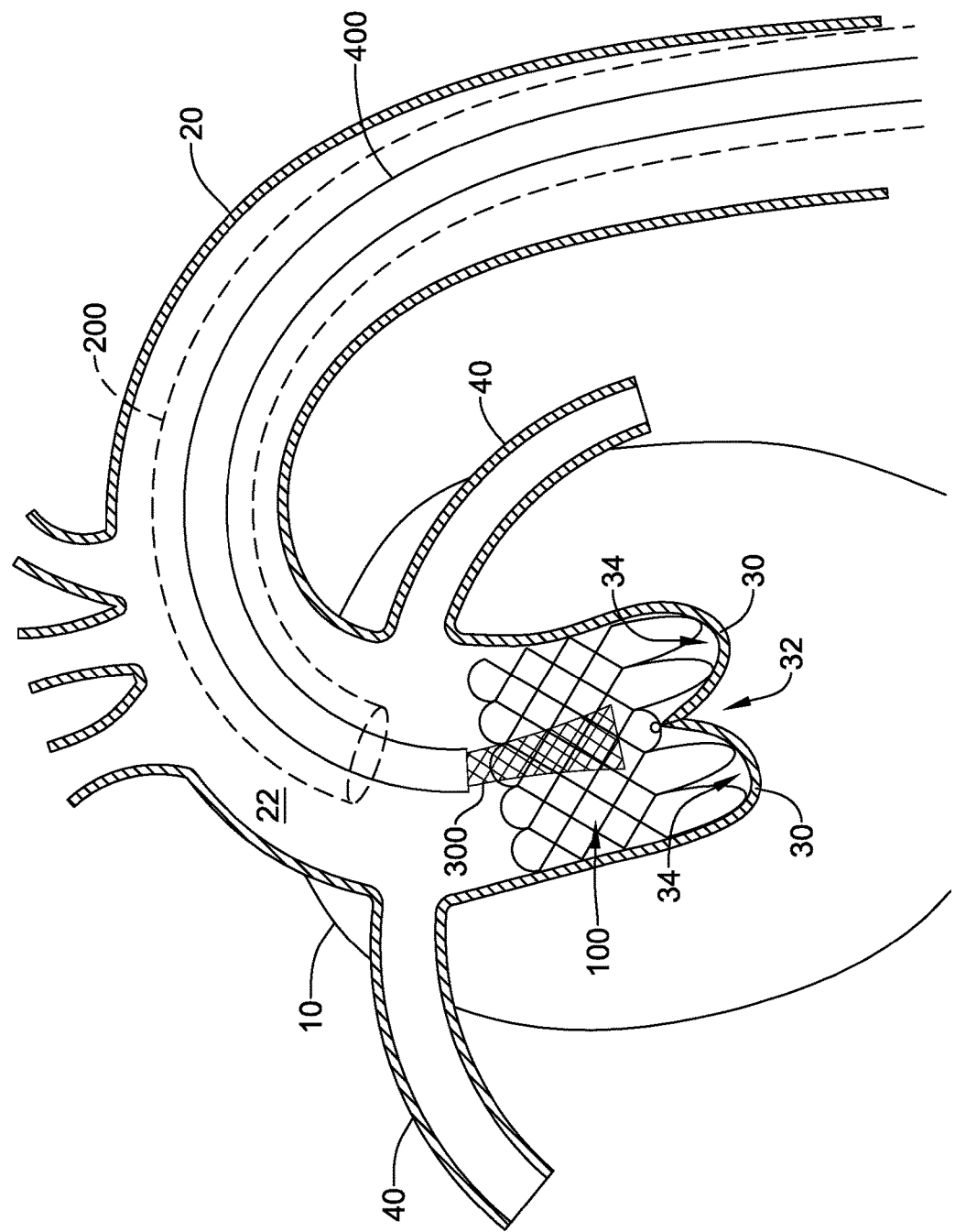

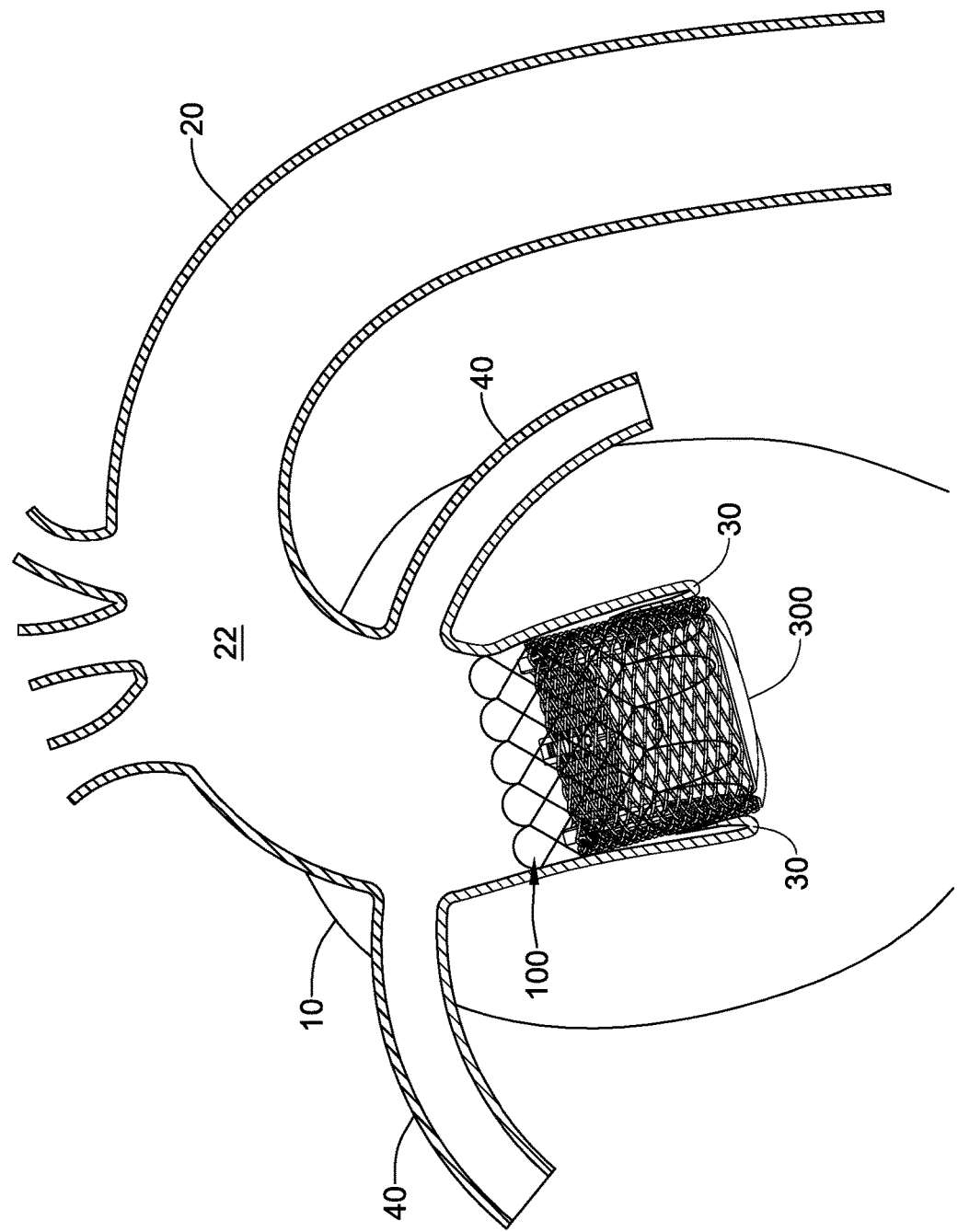

TAVI ANCHORING ASSIST DEVICE

CROSS-REFERENCE TO RELATED APPLICATIONS

This application claims the benefit of U.S. Provisional Application No. 62/129,184, filed Mar. 6, 2015 and U.S. Provisional Application No. 62/204,090, filed Aug. 12, 2015.

TECHNICAL FIELD

The disclosure is directed to an anchoring assistance device, such as a stent, for aiding in the anchoring of a medical implant in a body lumen. More particularly, the disclosure is directed to an anchoring assistance device configured to fortify the body lumen to provide a stable foundation for deployment of a medical implant.

BACKGROUND

A medical implant may be configured to be positioned in a body lumen for a variety of medical applications. For example, a medical implant may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. In some cases, a medical implant may be expanded and/or anchored against a wall or surface of a body lumen. However, some medical implants may be prone to migrate through the body lumen if the wall of the body lumen fails to provide a stable foundation for an outward radial force to anchor the medical implant.

Accordingly, it may be desirable to provide endoprostheses or anchoring assistance devices that may enhance the anchoring feature(s) of a medical implant, while providing flexibility in positioning of the anchoring assistance devices.

SUMMARY

The disclosure is directed to several alternative designs, materials and methods of manufacturing medical device structures and assemblies, and uses thereof.

In a first aspect, an anchoring assistance device may comprise an expandable scaffold including a mid-body section defining a central longitudinal axis, the expandable scaffold having a cusp interface section extending axially from a distal end of the mid-body section, and a crown end arrangement extending axially from a proximal end of the mid-body section. The expandable scaffold may be configured to expand radially outward from a delivery configuration to a deployed configuration. The cusp interface section may include a plurality of loop portions arranged at radial intervals about the central longitudinal axis of the expandable scaffold, each loop portion being configured to be positioned adjacent a leaflet of an aortic valve. Each loop portion may be circumferentially spaced apart from another loop portion by a region having a deployment ring, the region being configured to span a commissure of the aortic valve and extending distally a shorter distance from the distal end than the loop portions.

In addition or alternatively, and in a second aspect, each loop portion includes two cusp loops.

In addition or alternatively, and in a third aspect, each region includes a minor loop, each minor loop having the deployment ring coupled thereto.

In addition or alternatively, and in a fourth aspect, the two cusp loops circumferentially overlap distal of the minor loops in the deployed configuration.

In addition or alternatively, and in a fifth aspect, the two cusp loops are circumferentially spaced apart from each other distal of the minor loops in the deployed configuration.

In addition or alternatively, and in a sixth aspect, each deployment ring is formed from a coiled loop portion of its minor loop.

In addition or alternatively, and in a seventh aspect, each deployment ring is integrally formed with its minor loop.

In addition or alternatively, and in an eighth aspect, each loop portion extends a longer circumferential distance around the central longitudinal axis than each region.

In addition or alternatively, and in a ninth aspect, the anchoring assistance device includes an equal number of loops portions and regions.

In addition or alternatively, and in a tenth aspect, an anchoring assistance device delivery system may comprise a delivery sheath having at least one lumen extending longitudinally therethrough and an actuator mechanism disposed at a proximal end of the delivery sheath. The anchoring assistance device delivery system may also comprise an elongate deployment member extending from the actuator mechanism to an anchoring assistance device disposable within a distal portion of the delivery sheath. The anchoring assistance device may comprise an expandable scaffold including a mid-body section defining a central longitudinal axis, the expandable scaffold having a cusp interface section extending axially from a distal end of the mid-body section, and a crown end arrangement extending axially from a proximal end of the mid-body section. The expandable scaffold may be configured to expand radially outward from a delivery configuration to a deployed configuration. The cusp interface section may include a plurality of loop portions arranged at radial intervals about the central longitudinal axis of the expandable scaffold, each loop portion being configured to be positioned adjacent a leaflet of an aortic valve. Each loop portion may be circumferentially spaced apart from another loop portion by a region having a deployment ring, the region being configured to span a commissure of the aortic valve and extending distally a shorter distance from the distal end than the loop portions. The elongate deployment member may be configured to releasably engage with the deployment rings such that the elongate deployment member actuates the expandable scaffold from the delivery configuration to the deployed configuration in response to activation of the actuator mechanism.

In addition or alternatively, and in an eleventh aspect, the actuator mechanism is configured to axially translate the elongate deployment member with respect to the delivery sheath.

In addition or alternatively, and in a twelfth aspect, the elongate deployment member includes a plurality of deployment loops at a distal end thereof, each deployment loop being configured to releasably engage with one deployment ring.

In addition or alternatively, and in a thirteenth aspect, each deployment loop extends at least partially through one deployment ring.

In addition or alternatively, and in a fourteenth aspect, proximal withdrawal of the elongate deployment member creates an interference between each deployment loop and its corresponding deployment ring such that the expandable scaffold is actuated from the delivery configuration to the deployed configuration.

In addition or alternatively, and in a fifteenth aspect, after achieving the deployed configuration, further proximal withdrawal of the elongate deployment member pulls each deployment loop through its corresponding deployment ring to disengage the elongate deployment member from the expandable scaffold.

In addition or alternatively, and in a sixteenth aspect, a medical implant system may comprise a delivery sheath having at least one lumen extending longitudinally therethrough and an actuator mechanism disposed at a proximal end of the delivery sheath. The medical implant system may also comprise an anchoring assistance device comprising an expandable scaffold including a mid-body section defining a central longitudinal axis, the expandable scaffold having a cusp interface section extending axially from a distal end of the mid-body section, and a crown end arrangement extending axially from a proximal end of the mid-body section. The medical implant system may also comprise a replacement heart valve implant. The expandable scaffold may be configured to expand radially outward from a delivery configuration to a deployed configuration. The cusp interface section may include a plurality of loop portions arranged at radial intervals about the central longitudinal axis of the expandable scaffold, each loop portion being configured to be positioned adjacent a leaflet of an aortic valve. Each loop portion may be circumferentially spaced apart from another loop portion by a region having a deployment ring, the region being configured to span a commissure of the aortic valve and extending distally a shorter distance from the distal end than the loop portions. An elongate deployment member may extend from the actuator mechanism to the anchoring assistance device, the anchoring assistance device being disposable within a distal portion of the delivery sheath. The elongate deployment member may be configured to releasably engage with the deployment rings to actuate the expandable scaffold from the delivery configuration to the deployed configuration. The replacement heart valve implant may be configured to be at least partially disposed within the expandable scaffold in the deployed configuration.

In addition or alternatively, and in a seventeenth aspect, the replacement heart valve implant includes a transcatheter aortic valve implantation (TAVI) device or a transcatheter aortic valve replacement (TAVR) device.

In addition or alternatively, and in an eighteenth aspect, the replacement heart valve implant includes an anchor member expandable from a collapsed configuration to an installed configuration, the anchor member being configured to radially engage the expandable scaffold in the installed configuration.

In addition or alternatively, and in a nineteenth aspect, the anchoring assistance device prevents migration of the replacement heart valve implant when the anchor member is radially engaged with the expandable scaffold.

In addition or alternatively, and in a twentieth aspect, the elongate deployment member includes a plurality of deployment loops at a distal end thereof, each deployment loop being configured to releasably engage with one deployment ring. Proximal withdrawal of the elongate deployment member may create an interference between each deployment loop and its corresponding deployment ring such that the expandable scaffold is actuated from the delivery configuration to the deployed configuration.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The aspects of the disclosure may be more completely understood in consideration of the following detailed description of various embodiments in connection with the accompanying drawings, in which:

FIGS. 8-9 illustrate aspects of delivering an example medical implant into an example anchoring assistance device within a body lumen;

FIGS. 20-21 illustrate aspects of delivering an example medical implant into an example anchoring assistance device within a body lumen.

Figure 1:
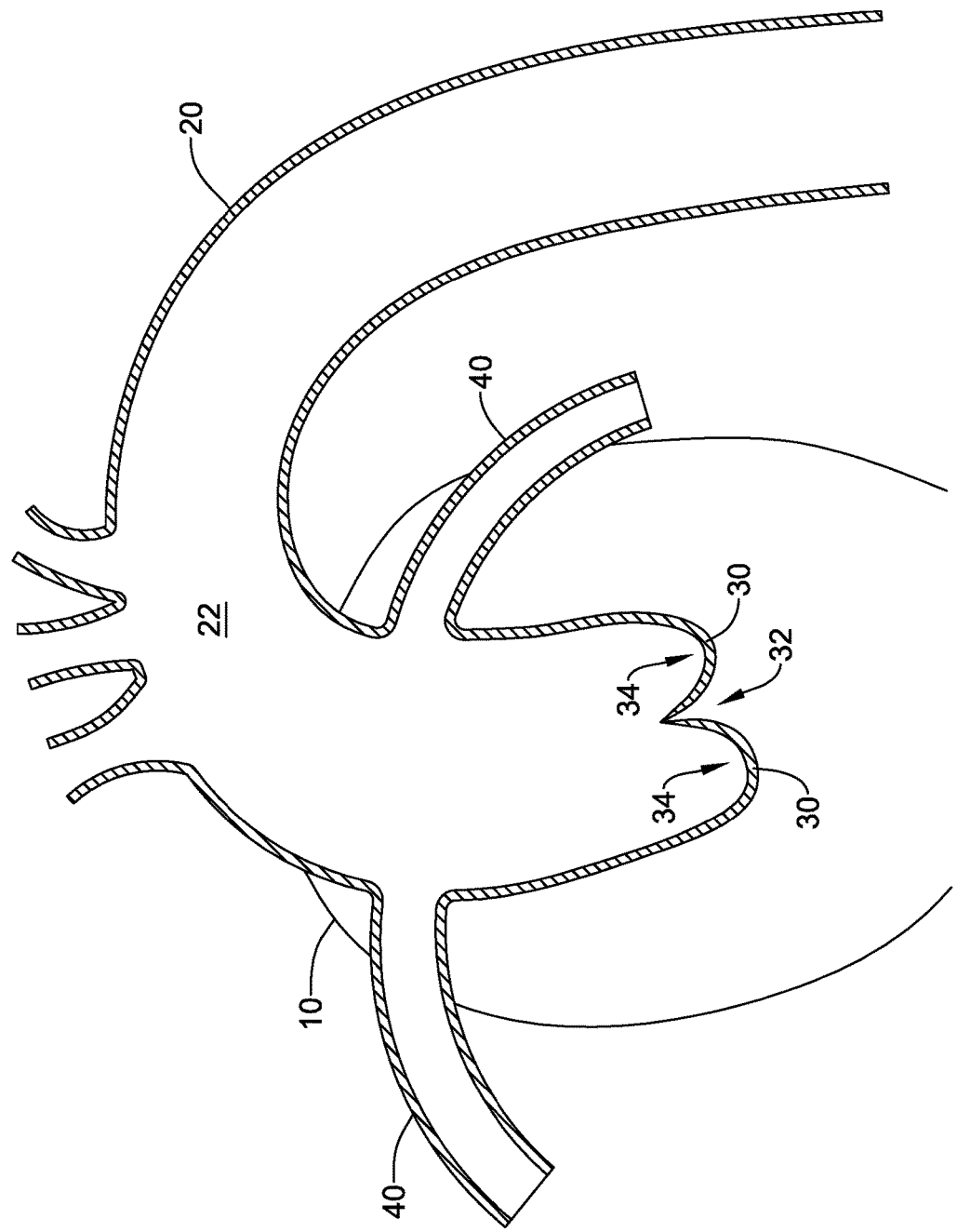
FIG. 1 is a schematic view of a portion of a heart and certain connected vasculature.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream" and "downstream" refer to a direction of fluid flow within a lumen, such as a body lumen or blood vessel.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The terms "transaortic valve implantation" and "transcatheter aortic valve implantation" may be used interchangeably, and may each be referred to using the acronym "TAVI".

The terms "transaortic valve replacement" and "transcatheter aortic valve replacement" may be used interchangeably, and may each be referred to using the acronym "TAVR".

FIG. 1 illustrates a schematic view of a portion of a patient's heart 10 and certain connected vasculature, such as the aorta 20 connected to the heart 10 by the aortic arch 22, and the coronary arteries 40. Leaflets 30 of an aortic valve may be seen schematically where the aorta 20 meets and/or joins the heart 10. On a downstream side of the leaflets 30 is an area described herein as a cusp 34, where the cusp 34 is a space between the leaflets 30 and a wall of the aorta 20 and/or the aortic arch 22 immediately downstream of and/or adjacent to the aortic valve. The leaflets 30 meet or intersect at a commissure 32. As such, is a tricuspid heart valve, such as a normal aortic valve, three commissures 32 will be present with three cusps 34 disposed therebetween. In a bicuspid heart valve, two commissures 32 will be present with two cusps 34 disposed therebetween.

Figure 2:
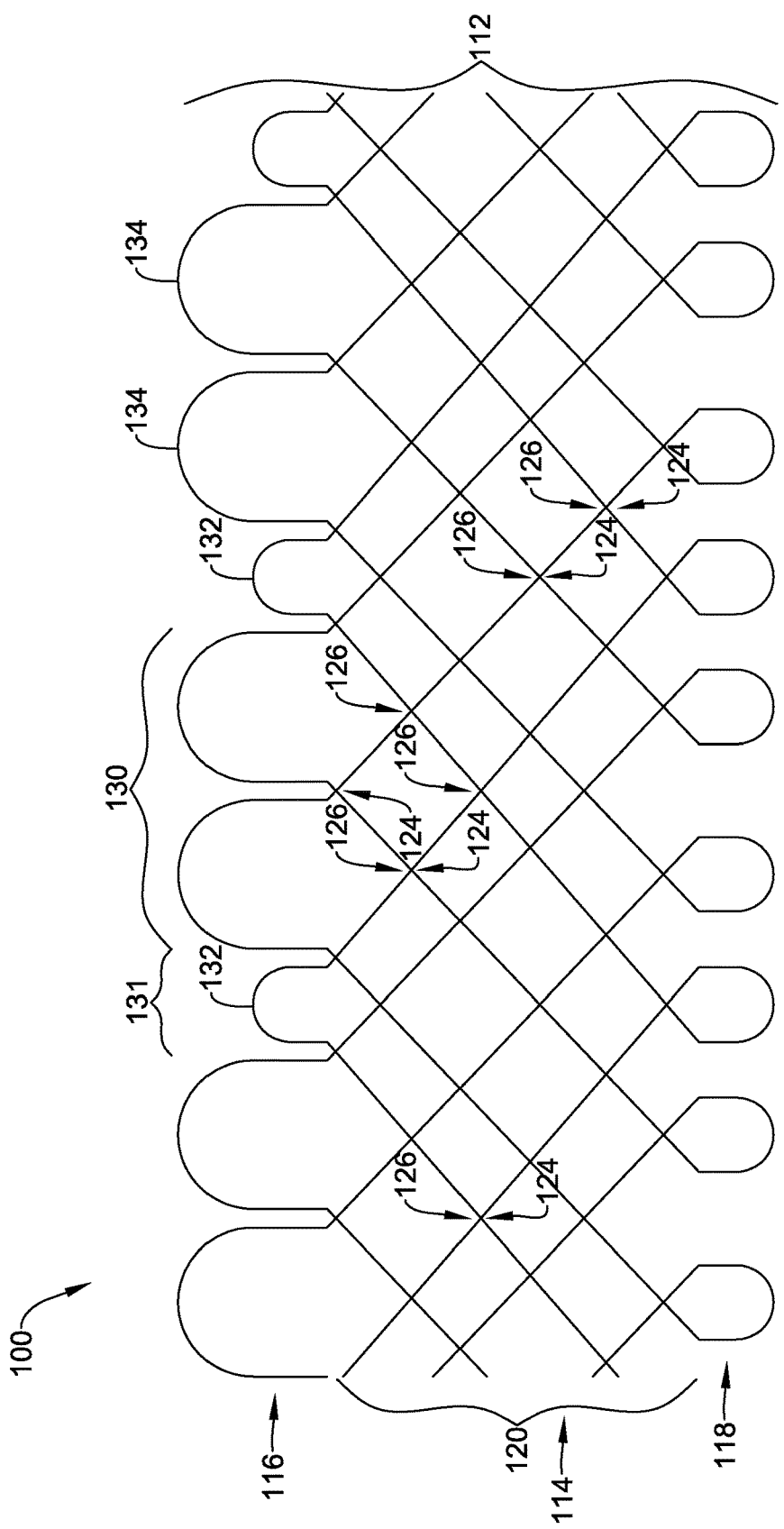
FIG. 2 is a flat pattern view of an example anchoring assistance device.
Figure 10:
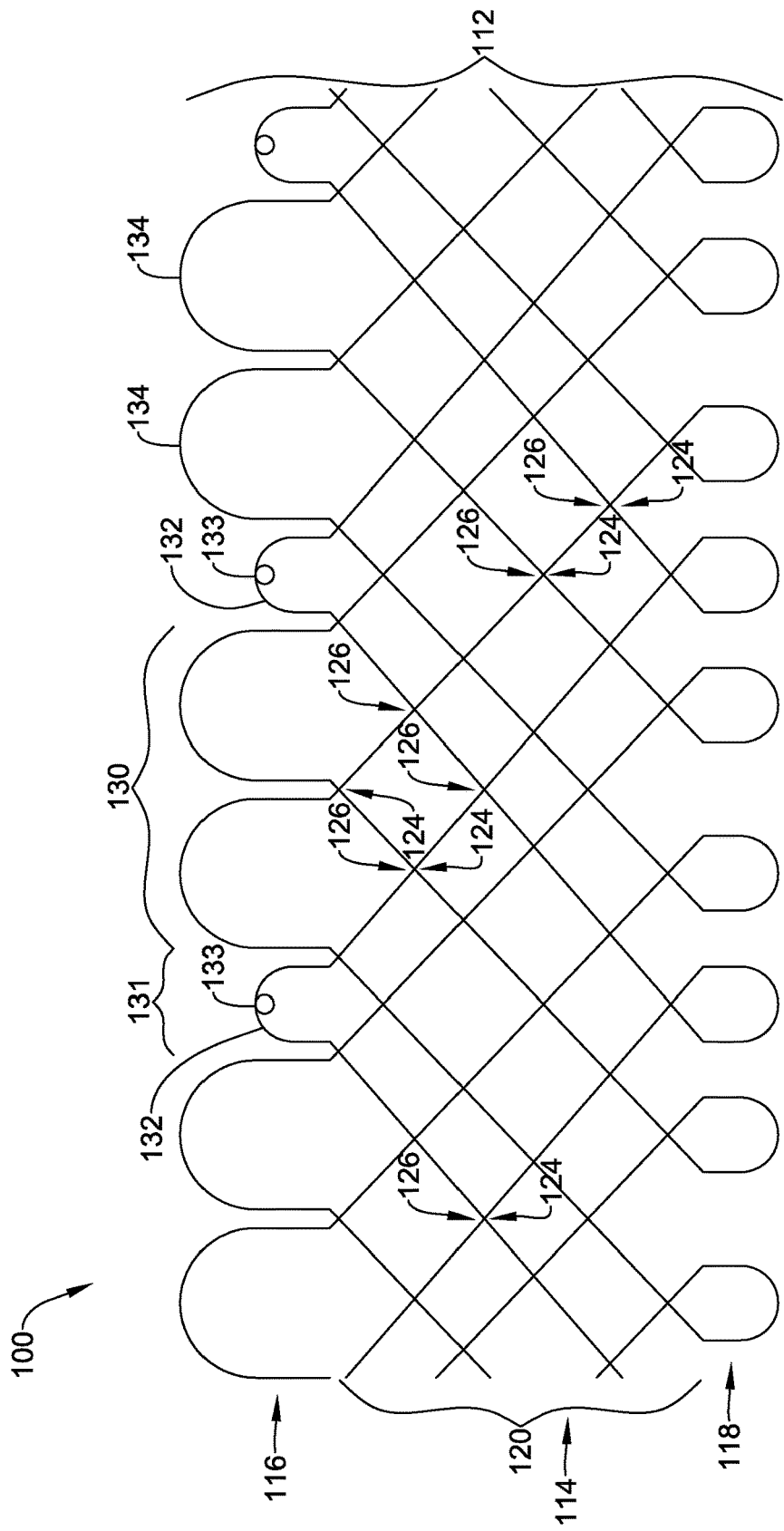
FIG. 10 is a flat pattern view of an example anchoring assistance device.

An exemplary implantable anchoring assistance device 100, shown in a flat pattern view in FIGS. 2 and 10 for example, may be configured to be positioned in a body lumen for a variety of medical applications. For example, the anchoring assistance device 100 may be used to treat a stenosis in a blood vessel, used to maintain a fluid opening or pathway in the vascular, urinary, biliary, tracheobronchial, esophageal, or renal tracts, or position a device such as an artificial or replacement valve or filter within a body lumen, in some instances. In some instances, the anchoring assistance device 100 may be a prosthetic graft, a stent-graft, or a stent (e.g., a vascular stent, tracheal stent, bronchial stent, esophageal stent, etc.). Although illustrated herein as a stent or stent-like structure, the anchoring assistance device 100 may be any of a number of devices that may be introduced endoscopically, subcutaneously, percutaneously, and/or surgically to be positioned within an organ, tissue, or body lumen, such as a heart, artery, vein, urethra, esophagus, trachea, bronchus, bile duct, or the like.

In some embodiments, the anchoring assistance device 100 may be a self-expanding anchoring assistance device configured to automatically expand from a delivery configuration to a deployed configuration upon the removal of a constraining force acting on the anchoring assistance device. In other embodiments, the anchoring assistance device 100 may be a mechanically expandable anchoring assistance device configured to be expanded from a delivery configuration to a deployed configuration through the application of a mechanical force acting on the anchoring assistance device (e.g., a radially expanding balloon or actuation of a deployment member). In some embodiments, an anchoring assistance device combining any, some, or all elements of a self-expanding anchoring assistance device and a mechanically expandable anchoring assistance device may be utilized.

In some embodiments, the anchoring assistance device 100 may be a generally tubular member formed from an expandable scaffold 112 having a mid-body section 114 defining a central longitudinal axis. In some embodiments, the expandable scaffold 112 may include a cusp interface section 116 extending axially or longitudinally in a distal direction from a distal end of the mid-body section 114. In some embodiments, the expandable scaffold 112 may include a crown end arrangement 118 extending axially or longitudinally in a proximal direction from a proximal end of the mid-body section 114.

In some embodiments, the expandable scaffold 112 may include an outer surface defining an outer diameter, and an inner surface defining an inner diameter and/or a lumen extending through the expandable scaffold 112 along the central longitudinal axis. In some embodiments, the mid-body section 114 of the expandable scaffold 112 may include a plurality of strut rows 120 arranged along the length of the anchoring assistance device 100. In some instances, the plurality of strut rows 120 may extend circumferentially around a perimeter of the expandable scaffold 112.

As used herein, the outer surface of the expandable scaffold 112 is intended to refer to a radially outward facing surface of the plurality of strut rows 120 commensurate with the outer diameter of the expandable scaffold 112 and/or the anchoring assistance device 100. As used herein, the inner surface of the expandable scaffold 112 is intended to refer to a radially inward facing surface of the plurality of strut rows 120 commensurate with the inner diameter and/or the lumen of the expandable scaffold 112 and/or the anchoring assistance device 100.

In some embodiments, the plurality of strut rows 120 may include two, three, four, five, six, or more strut rows arranged along the length of the expandable scaffold 112. In some embodiments, adjacent strut rows may define a gap or interstice therebetween, each gap or interstice having a length along the central longitudinal axis and spacing the adjacent strut rows 120 apart by the gap or interstice. Thus, the length of the anchoring assistance device 100 may be dictated, at least in part, by the number of strut rows 120 and/or the length(s) of the gaps or interstices. In some embodiments, some or all of the plurality of strut rows 120 may be immediately adjacent each other with no gap or interstice therebetween, and thus in some embodiments, may be connected directly together. In at least some embodiments, the expandable scaffold 112 and/or the mid-body section 114 may be formed as a cross-patterned braid or similar structure formed from a plurality of individual filaments.

In some embodiments, each strut row 120 may include continuously undulating struts defining interstitial spaces or openings therebetween. In some embodiments, each strut row 120 may include a plurality of intersecting struts or filaments. The struts of each strut row 120 may include alternating peaks 124 and valleys 126, the peaks 124 and valleys 126 corresponding to where individual segments of the struts intersect, converge, and/or diverge. The peaks 124 associated with a strut row 120 are located toward a first end of the expandable scaffold 112 while the valleys 126 associated with a strut row 120 are located toward a second opposite end of the expandable scaffold 112. In some embodiments, the peaks 124 of one strut row 120 may be connected directly to the valleys 126 of an adjacent strut row 120, and vice versa.

The anchoring assistance device 100 may be formed of any desired material, such as a biocompatible material including biostable, bioabsorbable, biodegradable, and/or bioerodible materials. For instance, the anchoring assistance device 100 may be formed of a metallic material, a polymeric material, or suitable combinations thereof. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof. Some suitable polymeric materials include, but are not necessarily limited to, polyamide, polyether block amide, polyethylene, polyethylene terephthalate, polypropylene, polyvinylchloride, polyurethane, polytetrafluoroethylene, polysulfone, and copolymers, blends, mixtures or combinations thereof.

In some instances, the expandable scaffold 112 of the anchoring assistance device 100 may be formed as a monolithic structure from a single tubular member, such as a metallic tube. For example, the expandable scaffold 112 may be cut (e.g., laser cut) from a single metallic tubular member and then expanded. Thus, the plurality of strut rows 120 of the expandable scaffold 112 may be formed as a monolithic structure cut from a single metallic tube, in some instances. In some instances, the plurality of strut rows 120 of the expandable scaffold 112 may be cut from a single polymeric tubular member. In some embodiments, the expandable scaffold 112 may be machined, chemically etched, or otherwise formed as a monolithic structure from a single tubular member.

In some embodiments, the mid-body section 114 of the expandable scaffold 112 may be formed as a cross-patterned braid. In some embodiments, the cusp interface section 116 and the crown end arrangement 118 may be bonded, attached, joined, or otherwise connected to the mid-body section 114. In some embodiments, the cusp interface section 116 and the crown end arrangement 118 may be integrally and/or monolithically formed with the mid-body section 114. In some embodiments, the mid-body section 114, the cusp interface section 116, and/or the crown end arrangement 118 may be formed from different materials. In some embodiments, the mid-body section 114, the cusp interface section 116, and/or the crown end arrangement 118 may be formed from similar materials or the same material. In some embodiments, the expandable scaffold 112 may be formed, manufactured, or otherwise made by applying and/or positioning a plurality of individual filaments on or around a mandrel or other tool. In some embodiments, the cusp interface section 116 and/or the crown end arrangement 118 may be formed from the same plurality of filaments used to form the mid-body section 114.

In some embodiments, the crown end arrangement 118 may form a series of individual loops connecting adjacent filaments of the mid-body section 114, as seen in FIGS. 2 and 10, for example. In some embodiments, the series of individual loops of the crown end arrangement 118 may not overlap or intersect each other distal of the mid-body section 114. In some embodiments, the series of individual loops of the crown end arrangement 118 may overlap or intersect each other distal of the mid-body section 114. In some embodiments, the series of individual loops of the crown end arrangement 118 may extend proximally from the mid-body section 114 a shorter or smaller distance than the cusp interface section 116 extends distally from the mid-body section 114.

In some embodiments, the cusp interface section 116 may include a plurality of loop portions 130 arranged at radial intervals about the central longitudinal axis of the expandable scaffold 112. In some embodiments, the plurality of loop portions 130 of the cusp interface section 116 may include three loop portions 130 arranged at radial intervals about the central longitudinal axis of the expandable scaffold 112. In some embodiments, the plurality of loop portions 130 of the cusp interface section 116 may include two loop portions, three loops portions, four loop portion, five loop portions, six loop portions, or other suitable numbers or quantities of loop portions as desired. In some embodiments, the plurality of loop portions 130 may be arranged at substantially equal radial intervals about the central longitudinal axis of the expandable scaffold 112 (e.g., 180 degrees, 120 degrees, 90 degrees, 72 degrees, 60 degrees, etc.).

In some embodiments, each of the plurality of loop portions 130 (e.g., each of the three loop portions) may be circumferentially spaced apart from another loop portion 130 by a region 131 extending distally from the distal end of the mid-body section 114 a shorter distance from the distal end than the plurality of loop portions 130. In some embodiments, a region 131 may include a minor loop 132. In some embodiments, a region 131 has a deployment ring 133 and/or a minor loop 132 may include a deployment ring 133 coupled thereto. In some embodiments, each deployment ring 133 may be formed from a coiled loop portion of its minor loop 132. In some embodiments, each deployment ring 133 may be integrally formed with its minor loop 132.

In some embodiments, the anchoring assistance device 100 may include an equal number or quantity of loop portions 130 and regions 131 and/or minor loops 132. For example, in some embodiments, the expandable scaffold may include three loop portions 130 and three regions 131 and/or minor loops 132, each region 131 and/or minor loop 132 being disposed between two adjacent loop portions 130. In some embodiments, each loop portion 130 may extend a longer or greater circumferential distance around the central longitudinal axis than each region 131 and/or minor loop 132.

Figure 4:
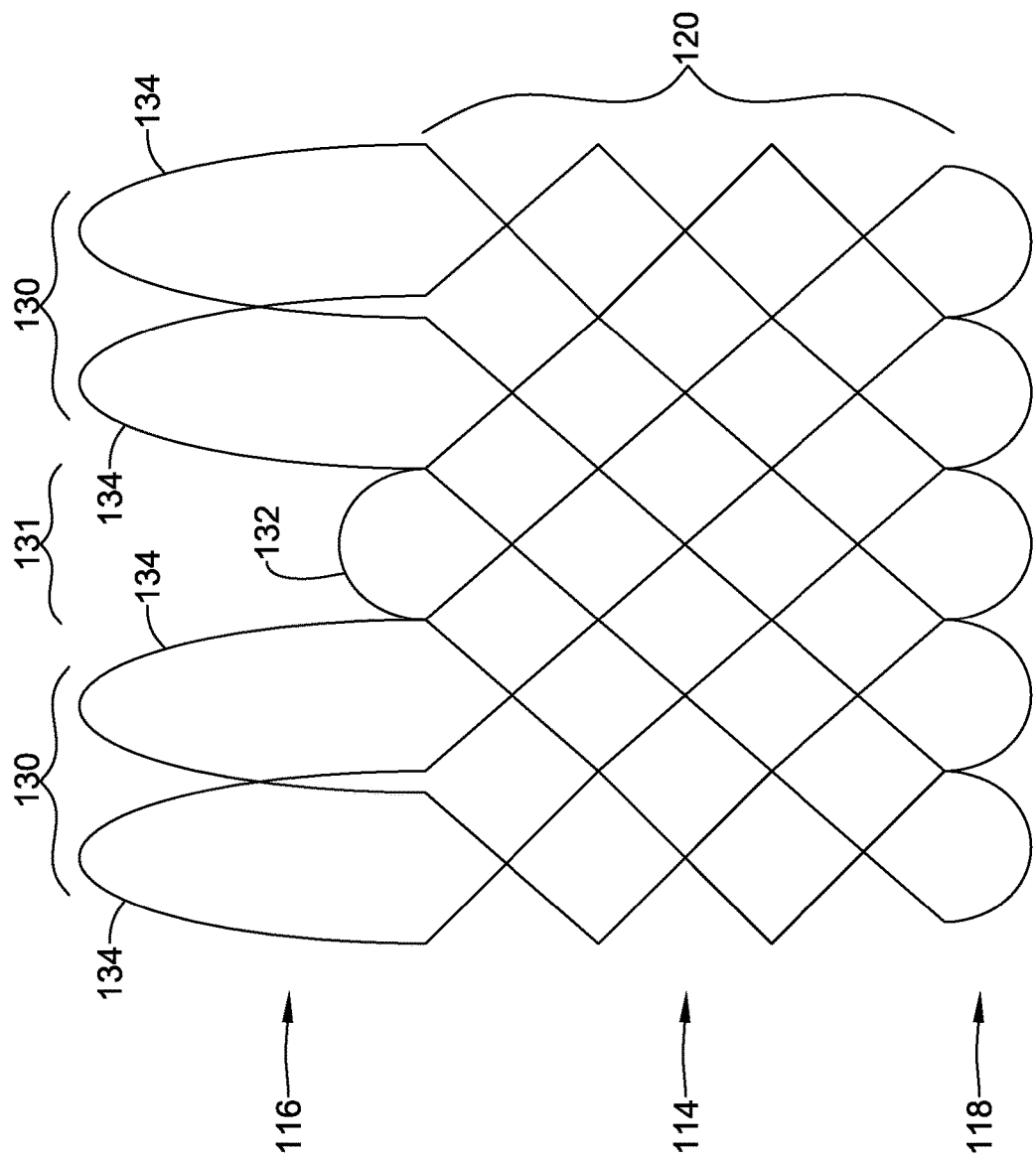
FIG. 4 is a partial side view of an example anchoring assistance device in a partially deployed configuration.
Figure 5:
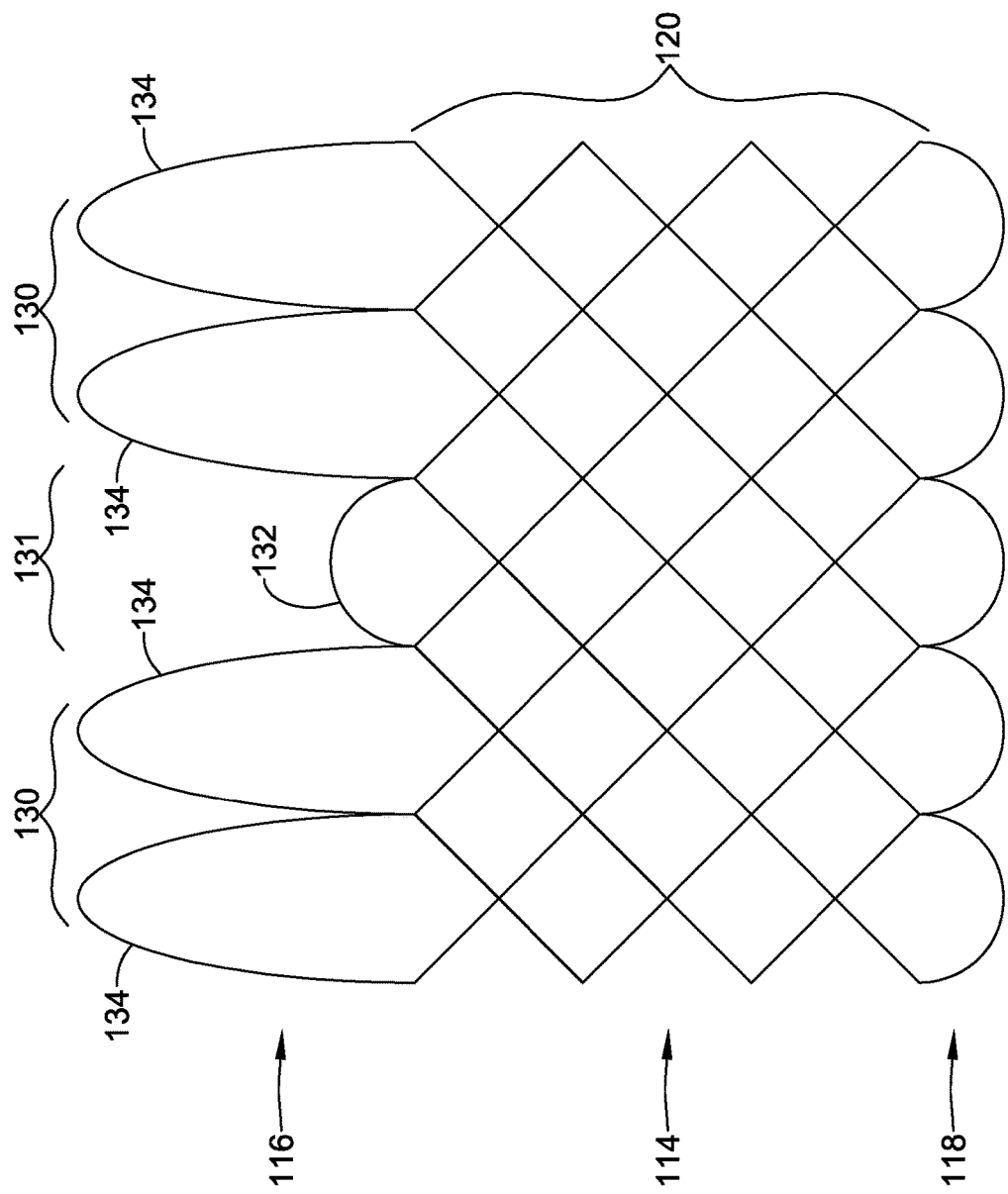
FIG. 5 is a partial side view of an example anchoring assistance device in a deployed configuration.
Figure 6:
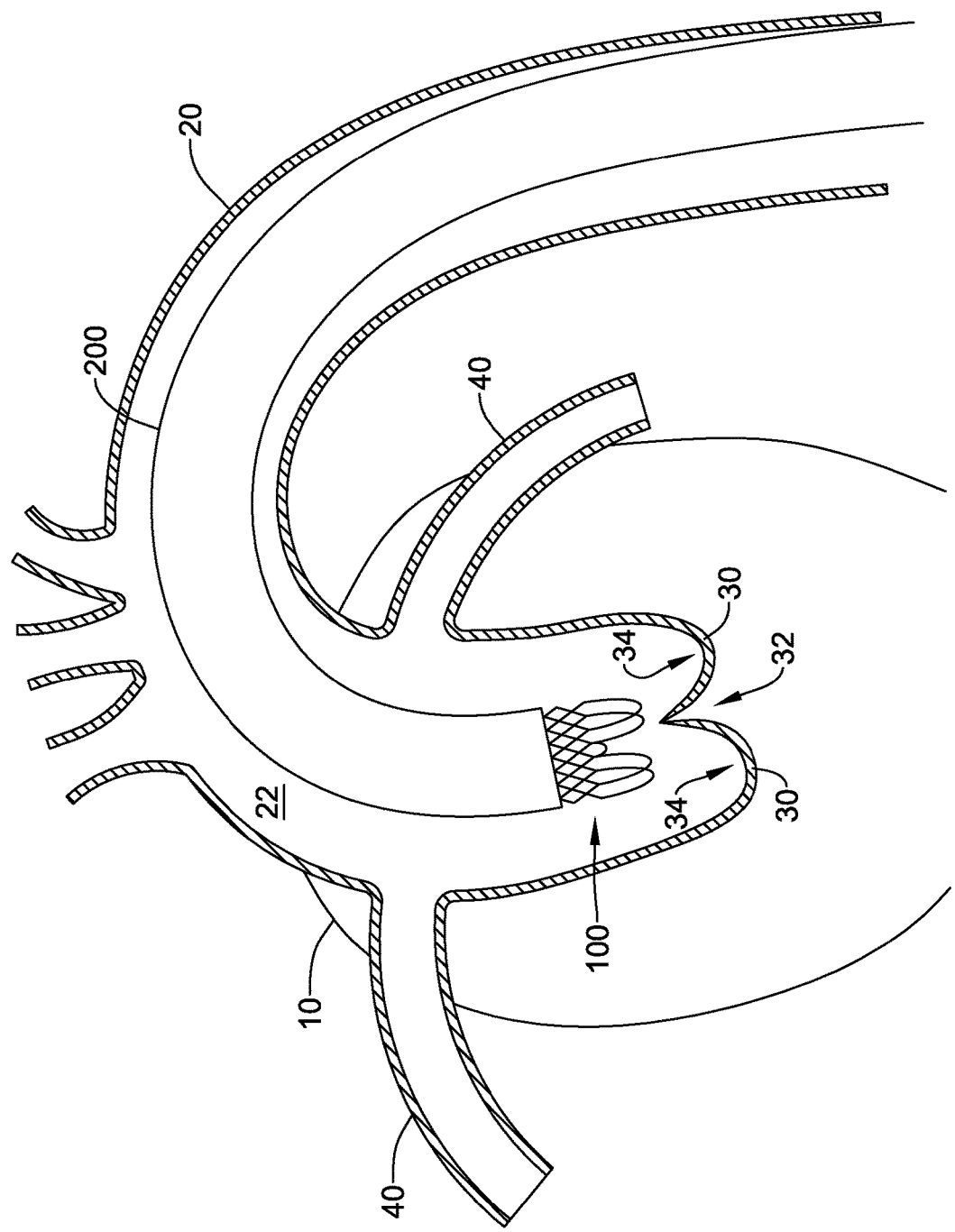
FIGS. 6-7 illustrate aspects of delivering an example anchoring assistance device into a body lumen.
Figure 7:
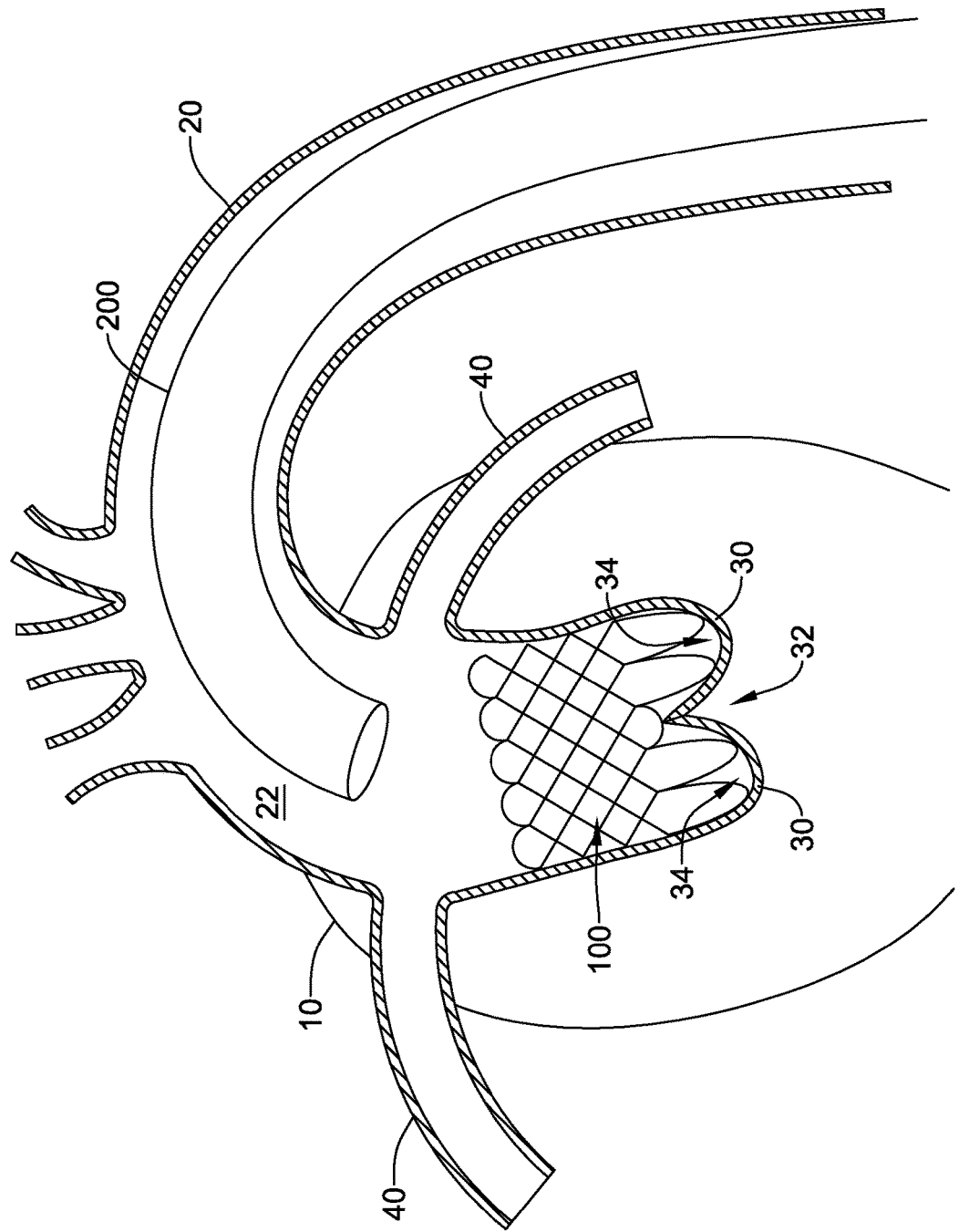
Figure 9B:
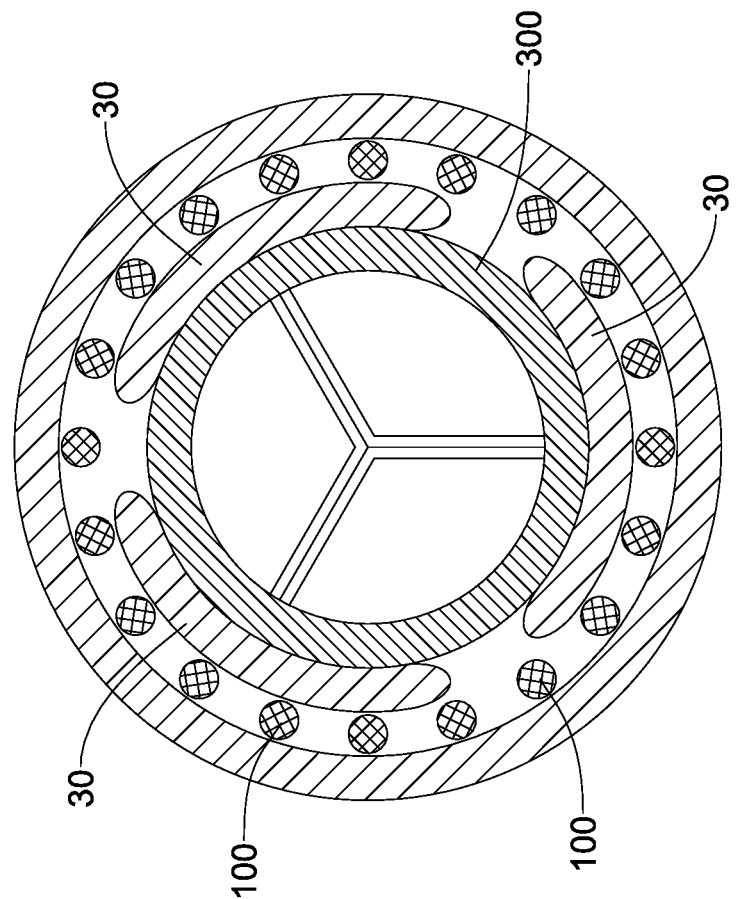
FIGS. 9A-9B are partial cross-sectional views of an example medical implant disposed within an example anchoring assistance device.
Figure 9A:
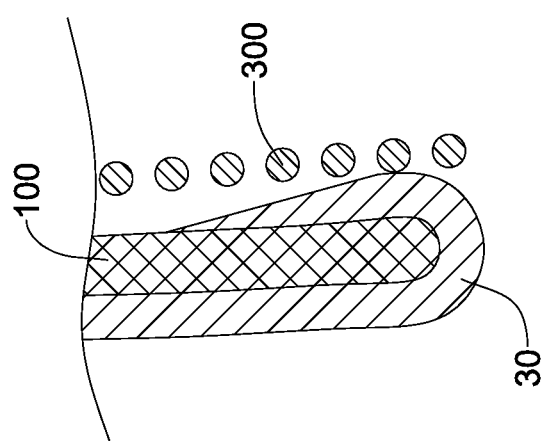
Figure 12:
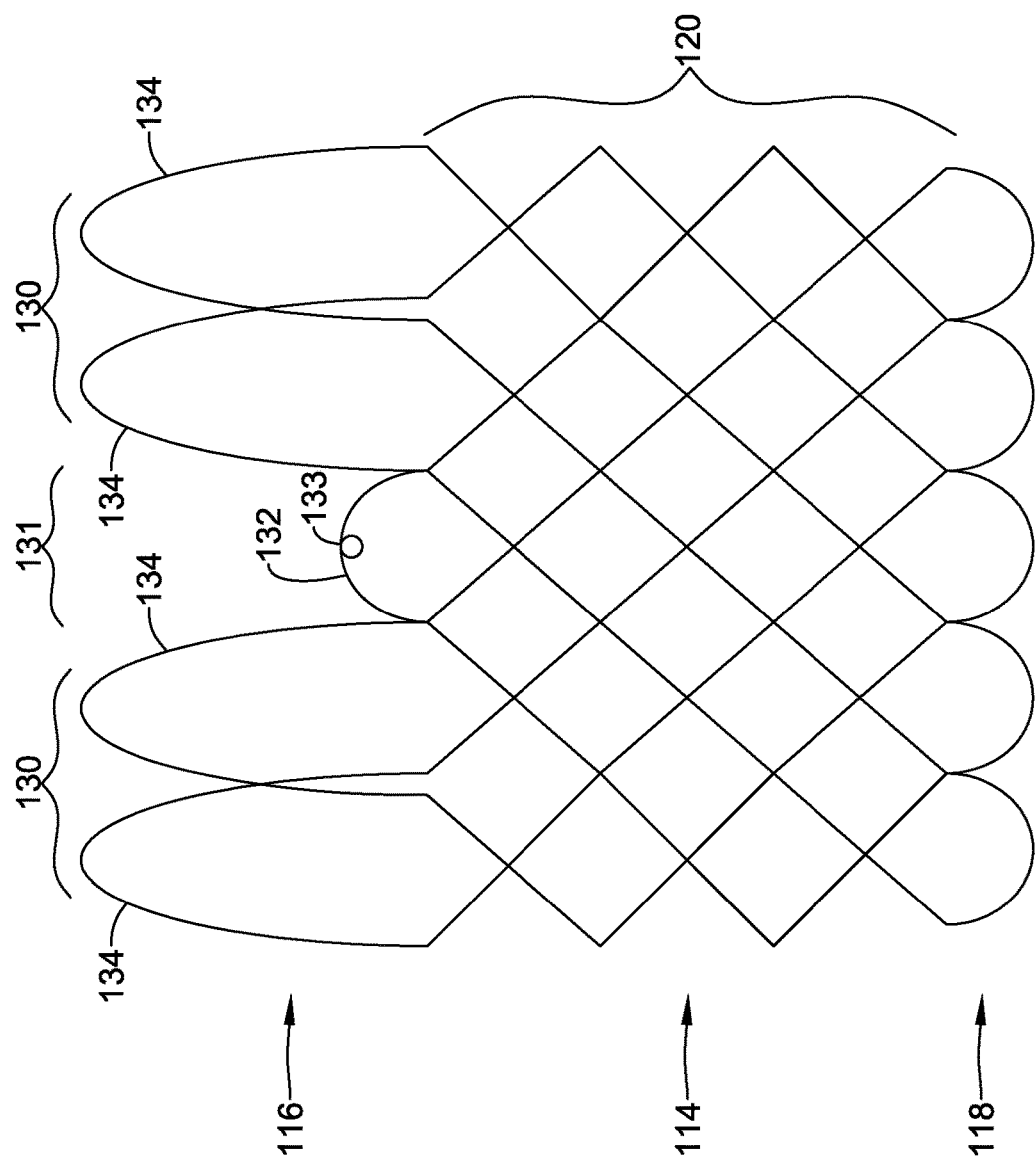
FIG. 12 is a partial side view of an example anchoring assistance device in a partially deployed configuration.
Figure 13:
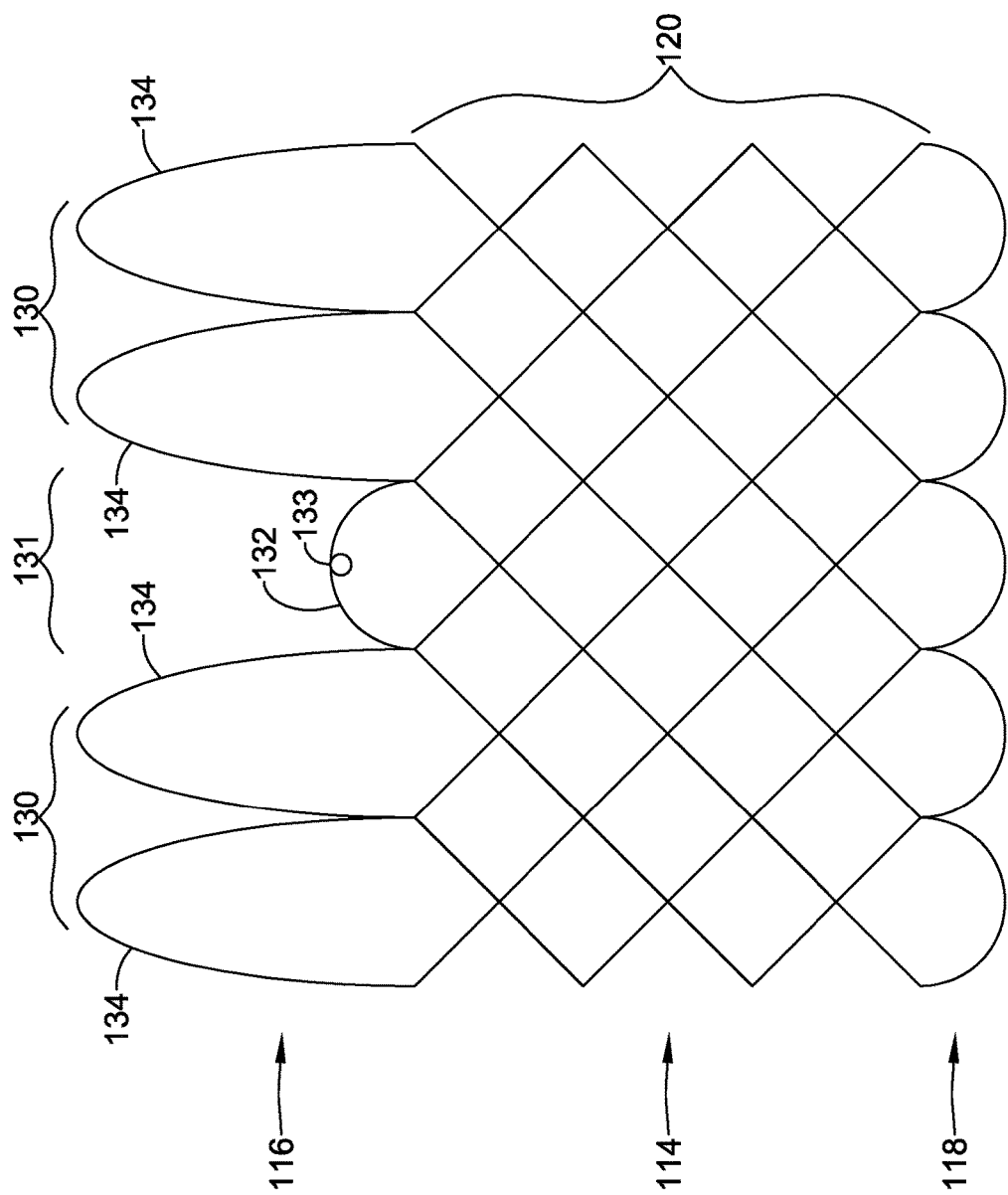
FIG. 13 is a partial side view of an example anchoring assistance device in a deployed configuration.

In some embodiments, each loop portion 130 may include two or more cusp loops 134. In some embodiments, each loop portion 130 may include two cusp loops 134. In some embodiments, each loop portion 130 may include three cusp loops, four cusp loops, five cusp loops, or other suitable numbers or quantities of cusp loops as desired. In some embodiments, at least a portion of each of the two or more cusp loops 134 (e.g., the two cusp loops 134) may circumferentially overlap distal of the region(s) 131 and/or the minor loop(s) 132 in the deployed configuration, as seen in FIGS. 4 and 12 for example, which in some embodiments may be considered to illustrate a partially deployed configuration. In some embodiments, the two or more cusp loops 134 (e.g., the two cusp loops 134) may be circumferentially spaced apart from each other distal of the region(s) 131 and/or the minor loop(s) 132 in the deployed configuration, as seen in FIGS. 5 and 13 for example. In other words, in some embodiments, any portion of the two or more cusp loops 134 disposed distal of the region(s) 131 and/or the minor loop(s) 132 may not circumferentially overlap each other. Different configurations (e.g., partial to complete or total deployment) of the plurality of loop portions 130 may permit a single size of anchoring assistance device 100 to be used in a number of different size body lumens.

Figure 3:
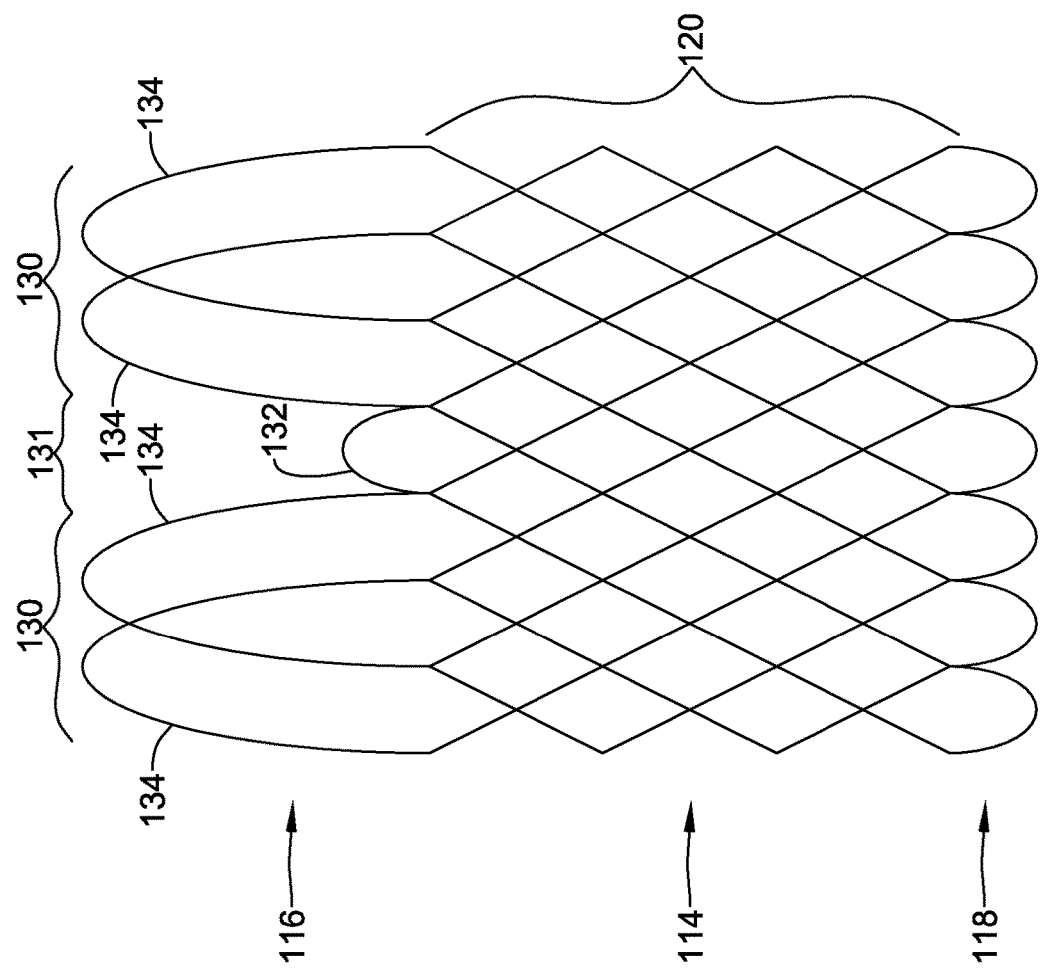
FIG. 3 is a partial side view of an example anchoring assistance device in a delivery configuration.
Figure 11:
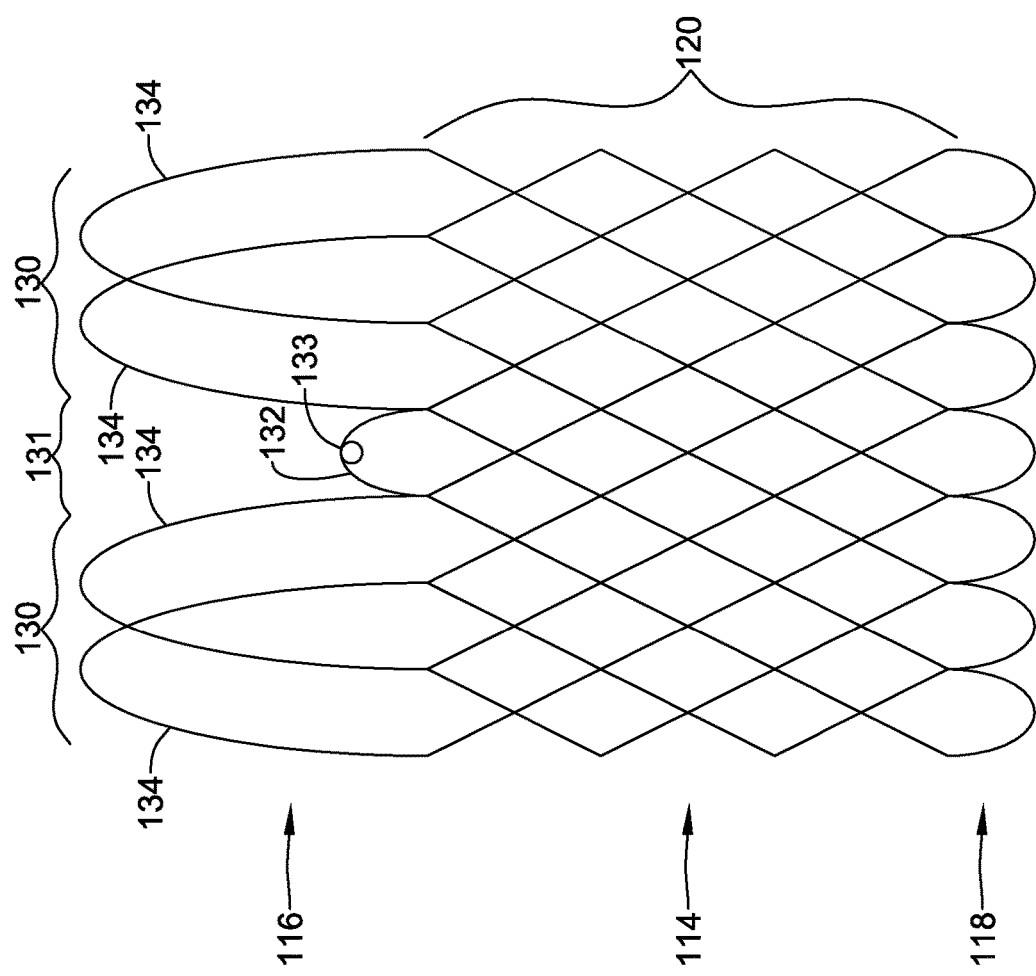
FIG. 11 is a partial side view of an example anchoring assistance device in a delivery configuration.

In use, an anchoring assistance device 100 may be advanced to a target site (e.g., a heart valve, an aortic valve, etc.) within a body lumen, such as a body lumen of the vascular, urinary, biliary, tracheobronchial, esophageal, or renal tracts. In some embodiments, the anchoring assistance device 100 may be advanced percutaneously through a patient's vasculature within a delivery sheath 200 in the delivery configuration (as seen in FIGS. 3 and 11 without the delivery sheath 200) through a patient's aorta 20, through the aortic arch 22, and into the cusps 34 and/or adjacent to the leaflets 30 of an aortic valve, which may be defective. As may be seen in FIGS. 6-7 and 15-19, after advancing the anchoring assistance device 100 and/or the delivery sheath 200 to the target site (e.g., within or adjacent to the aortic valve), the delivery sheath 200 may be retracted proximally relative to the anchoring assistance device 100 (and/or the anchoring assistance device 100 may be advanced distally relative to the delivery sheath 200) to deploy the anchoring assistance device 100 from the delivery configuration to the deployed configuration (such as described above) at the target site. Similarly, as seen in FIGS. 15-19, after releasing the anchoring assistance device 100 from the delivery sheath 200, an elongate deployment member 250 extending from an actuator mechanism 252 to the anchoring assistance device 100 may be actuated to axially translate the elongate deployment member 250 with respect to the delivery sheath 200 to actuate the anchoring assistance device 100 from the delivery configuration to the deployed configuration, as will be explained in more detail below.

In some embodiments, each loop portion 130 of the expandable scaffold 112 may be configured to be positioned immediately adjacent to and/or downstream of a heart valve (e.g., an aortic valve) in the deployed configuration (e.g., into the cusps 34 between the leaflets 30 and the wall of the aorta 20 and/or the aortic arch 22). In some embodiments, each region 131 and/or minor loop 132 may be configured to span and/or be positioned downstream and over a commissure 32 of the heart valve (e.g., aortic valve) in the deployed configuration. In at least some embodiments, the anchoring assistance device 100 may be disposed between the native aortic valve cusps 34 and/or leaflets 30 and the openings or ostia of the coronary arteries 40. In general, the anchoring assistance device 100 may be sized to avoid covering or overlapping an ostium of the coronary arteries 40.

In some embodiments, it may be beneficial to deploy a medical implant (e.g., a replacement heart valve implant) within the anchoring assistance device 100, as illustrated in FIGS. 8-9 and 20-21 for example. In some embodiments, a replacement heart valve implant 300 may be disposed within the delivery sheath 200 proximal of the anchoring assistance device 100. Further retraction of the delivery sheath 200 relative to the replacement heart valve implant 300 may deploy the replacement heart valve implant 300 from the delivery sheath 200. In some embodiments, after deployment of the anchoring assistance device 100, the delivery sheath 200 may be withdrawn from the target site and/or the patient's vasculature and a deployment sheath 400 as described herein may be advanced to the target site in its place. In some embodiments, a deployment sheath 400 may be extended and/or advanced through the delivery sheath 200, the deployment sheath 400 carrying a replacement heart valve implant 300 therein, as seen in FIGS. 8 and 20. In some embodiments, the replacement heart valve implant 300 may include or take the form of a transaortic valve implantation or transcatheter aortic valve implantation (TAVI) device or a transaortic valve replacement or transcatheter aortic valve replacement (TAVR) device. Following advancement of the deployment sheath 400 to the target site, the replacement heart valve implant 300 may then be deployed and/or disposed at least partially within the anchoring assistance device 100. In some embodiments, when the replacement heart valve implant 300 is expanded within the anchoring assistance device 100, the native heart valve leaflets 30 may be squeezed, pinched, trapped, or otherwise disposed between the anchoring assistance device 100 and the replacement heart valve implant 300, as seen in FIGS. 9, 9A, 9B, and 21.

A medical implant system may include an anchoring assistance device 100, such as that described above, and a replacement heart valve implant 300 at least partially disposed within the anchoring assistance device 100 in the deployed configuration. In at least some embodiments, the replacement heart valve implant 300 may include an anchor member 220 reversibly actuatable from a collapsed configuration to an installed configuration. In some embodiments, the anchor member 220 may be delivered though a deployment sheath 400 in the collapsed configuration, as seen in FIGS. 8 and 20. After deploying the replacement heart valve implant 300 from the deployment sheath 400, the anchor member 220 may be reversibly axially shortened and/or radially expanded from the collapsed configuration to the installed configuration. In at least some embodiments, the anchor member 220 may be configured to radially engage the expandable scaffold 112 when the anchor member 220 is in the installed configuration and the expandable scaffold 112 is in the deployed configuration, as seen in FIGS. 9 and 21. In some embodiments, the anchoring assistance device 100 may prevent migration of the replacement heart valve implant 300 when the anchor member 220 is radially engaged with the expandable scaffold 112.

FIG. 2 illustrates a flat pattern view of the expandable scaffold 112 of the anchoring assistance device 100. It is noted that the pattern shown in FIG. 2 is illustrated as if the expandable scaffold 112 were cut longitudinally and flattened, but one of skill in the art would understand that the pattern would extend circumferentially about the central longitudinal axis. As shown in FIG. 3, in the delivery configuration, the peaks 124 and valleys 126 of the plurality of strut rows 120 may be closely arranged.

Similarly, FIG. 10 illustrates a flat pattern view of the expandable scaffold 112 of the anchoring assistance device 100. It is noted that the pattern shown in FIG. 10 is illustrated as if the expandable scaffold 112 were cut longitudinally and flattened, but one of skill in the art would understand that the pattern would extend circumferentially about the central longitudinal axis. As shown in FIG. 11, in the delivery configuration, the peaks 124 and valleys 126 of the plurality of strut rows 120 may be closely arranged.

The anchoring assistance device 100 may be configured to engage a wall of a body lumen in the deployed configuration to inhibit migration of the anchoring assistance device 100 subsequent to implanting the anchoring assistance device 100 in the body lumen. For example, the anchoring assistance device 100 may engage the tissue between cartilage rings within the tracheal anatomy to provide anti-migration support for the anchoring assistance device 100. In at least some embodiments, the anchoring assistance device 100 may include one or more anchoring protrusions, hooks, barbs, or other similar features configured to engage and/or at least partially penetrate a wall of the body lumen.

In the deployed configuration, a space or opening may be defined between each of the struts of the plurality of strut rows 120. In some instances, the space or opening may be unobstructed by any other structure of the anchoring assistance device 100. In some instances, the space or opening may be configured to accept tissue ingrowth and/or the struts of the plurality of strut rows 120 may be configured to engage tissue or be encapsulated by tissue ingrowth. Accordingly, tissue ingrowth through the space or opening and covering or encapsulating the struts of the plurality of strut rows 120 subsequent to implanting the anchoring assistance device 100 may further secure the anchoring assistance device 100 in place within the patient's anatomy and thereby prevent migration of the anchoring assistance device 100.

As described above, each gap or interstice between adjacent strut rows 120 may have a length along the central longitudinal axis of the expandable scaffold 112 and may space the adjacent strut rows 120 apart. In some embodiments, the gaps or interstices between adjacent strut rows 120 may be defined by the valley(s) 126 of one strut row 120 and the peak(s) 124 of another strut row 120 immediately adjacent to the valley(s) 126. In some embodiments, the lengths of the gaps or interstices between adjacent strut rows 120 may vary along the length of the expandable scaffold 112.

As an example, in some embodiments, a first strut row 120 and a second strut row 120 may define a first gap or interstice therebetween, the second strut row 120 and a third strut row 120 may define a second gap or interstice therebetween, and the third strut row 120 and a fourth strut row 120 may define a third gap or interstice therebetween, wherein a length of the first interstice may be different from a length of the second interstice and/or a length of the third interstice may be different from the length of the second interstice. In one instance, a first interstice, a second interstice, and a third interstice may each be different lengths. In another instance, a first interstice may be shorter than a second interstice, which may be shorter than a third interstice. In yet another instance, a first interstice and a third interstice may be a same length that is a different length (e.g., shorter or longer) than a second interstice.

In some embodiments, an anchoring assistance device 100 may include a polymeric cover covering the struts of plurality of strut rows 120. In some embodiments, openings or spaces between the struts of the plurality of strut rows 120 are devoid of the polymeric cover and open to permit tissue ingrowth therethrough. The polymeric cover may be any desired polymeric coating, such as a polyurethane coating or silicone coating, for example. Other coatings and/or coating materials are also contemplated. In some instances, the polymeric cover may include a therapeutic agent embedded therein, disposed thereon, etc., if desired.

In some embodiments, the spaces or openings permit tissue ingrowth, while the polymeric cover prevents tissue ingrowth around and/or through other portions of the anchoring assistance device 100. Accordingly, subsequent to implantation of the anchoring assistance device 100, tissue may grow through the spaces or openings and thereby prevent migration of the implanted anchoring assistance device 100. However, in the event that it is desired to remove or reposition the anchoring assistance device 100 at a subsequent time after tissue ingrowth has occurred, the ingrown tissue can be cut away from the struts of the plurality of strut rows 120 and/or the struts of the plurality of strut rows 120 can be otherwise released from the ingrown tissue. Since the ingrown tissue is only located at discrete locations (e.g., at the spaces or openings), the procedure for removing the anchoring assistance device 100 may be less traumatic than if the tissue were ingrown throughout the entire expandable scaffold 112, such as with a bare or completely uncovered anchoring assistance device.

If it is desired to coat the expandable scaffold 112 with a polymeric cover, the polymeric cover may be applied to the expandable scaffold 112. For example, the expandable scaffold 112 may be coated with a polymeric cover by dipping the expandable scaffold 112 into a reservoir of a polymeric material solution. In other instances, a polymeric material solution may be sprayed onto the expandable scaffold 112, or otherwise applied to the expandable scaffold 112.

In some embodiments, a layer of the polymeric material solution may be formed across the expandable scaffold 112, covering the plurality of strut rows 120 and spanning the gaps or interstices between adjacent strut rows 120, as well as the spaces or openings between the struts of the plurality of strut rows 120. In some embodiments, the expandable scaffold 112 may be subjected to a process for selectively removing the layer of polymeric material solution from the spaces or openings between the struts of the plurality of strut rows 120 while retaining the polymeric material solution covering the struts of the plurality of strut rows 120 and spanning the gaps or interstices between adjacent strut rows 120.

For example, a fluid (e.g., air) may be blown toward the spaces or openings to selectively remove the coating from the spaces or openings. In other examples, the polymeric coating material extending across the spaces or openings may be mechanically popped or ruptured, or the surface tension of the polymeric coating material extending across the spaces or openings may be modified, such as chemically modified, to pop or rupture the polymeric coating material extending across the spaces or openings. In other examples, the polymeric coating material may be prevented from spanning the spaces or openings between the struts of the plurality of strut rows 120 while retaining the coating covering the struts of the plurality of strut rows 120 and spanning the gaps or interstices between adjacent strut rows 120. For example, the spaces or openings may be masked off prior to applying the polymeric coating material and then subsequently removed, or the struts of the plurality of strut rows 120 may be pre-treated, such as coated with a material, preventing wetting of the polymeric coating material across the spaces or openings when applying the polymeric coating material.

In some instances, a single layer of the polymeric coating may be applied to form the polymeric cover. In other instances, multiple layers of the polymeric coating may be applied to form the polymeric cover. The coating extending across the spaces or openings may be ruptured after each layer of the coating is applied or after multiple layers of the coating have been applied. For example, fluid may be blown toward the spaces or openings to rupture the coating extending across the spaces or openings after each layer of the coating is applied, or after multiple layers of the coating have been applied.

The polymeric material solution coating the expandable scaffold 112 may then be cured to form the polymeric cover disposed on the expandable scaffold 112. In some instances, the polymeric cover may extend the entire length of the expandable scaffold 112. In other instances, the polymeric cover may extend along only a portion of the length of the expandable scaffold 112, if desired.

Figure 14:
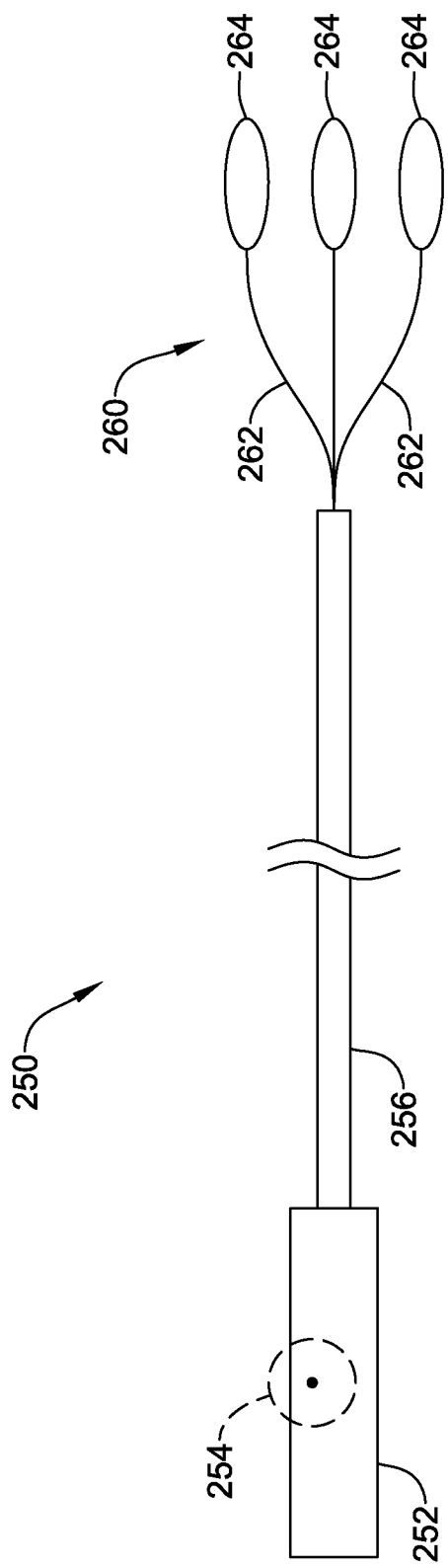
FIG. 14 is a schematic view of an example deployment mechanism for use with an anchoring assistance device of the current disclosure.
Figure 15:
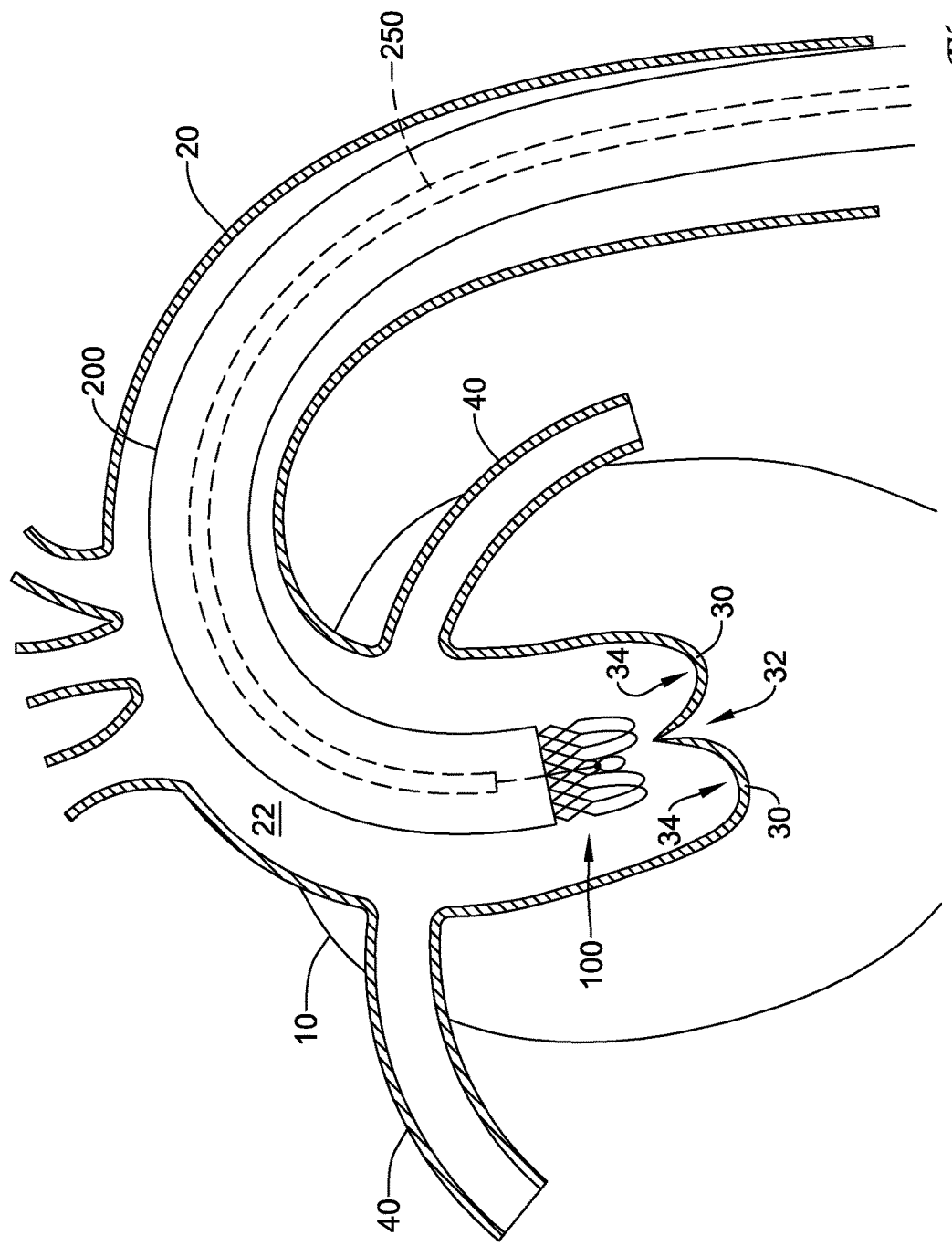
FIGS. 15-19 illustrate aspects of delivering an example anchoring assistance device into a body lumen.
Figure 16:
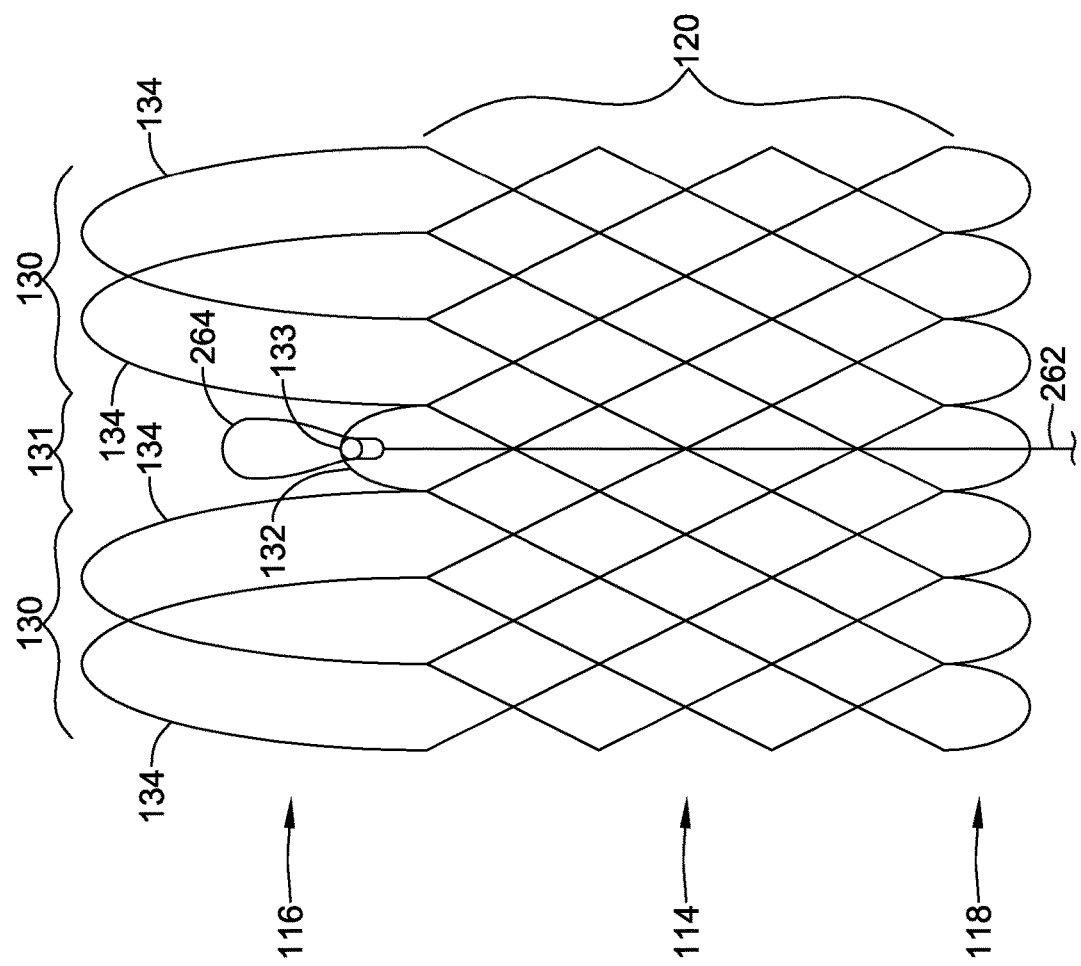
Figure 17:
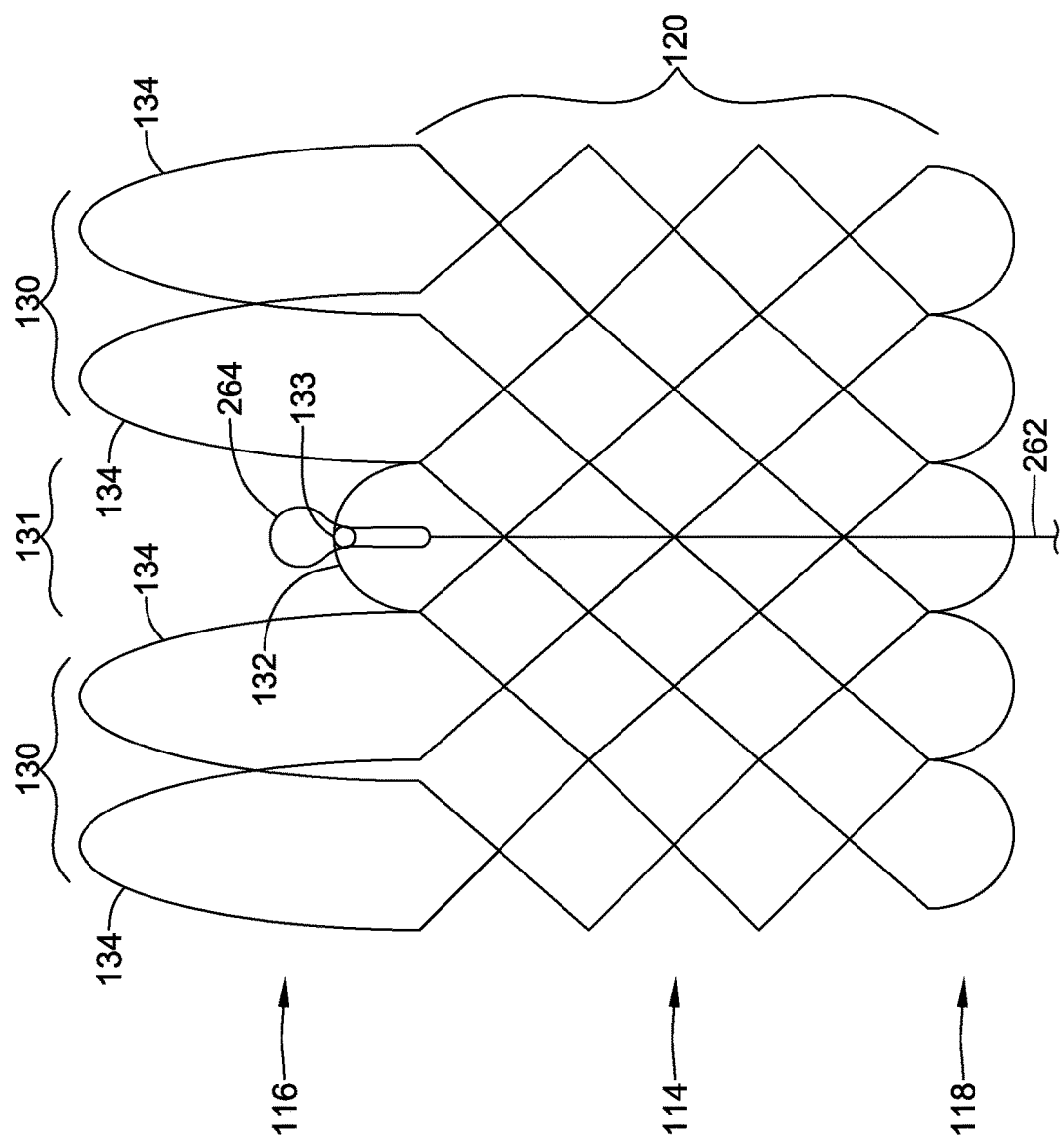
Figure 18:
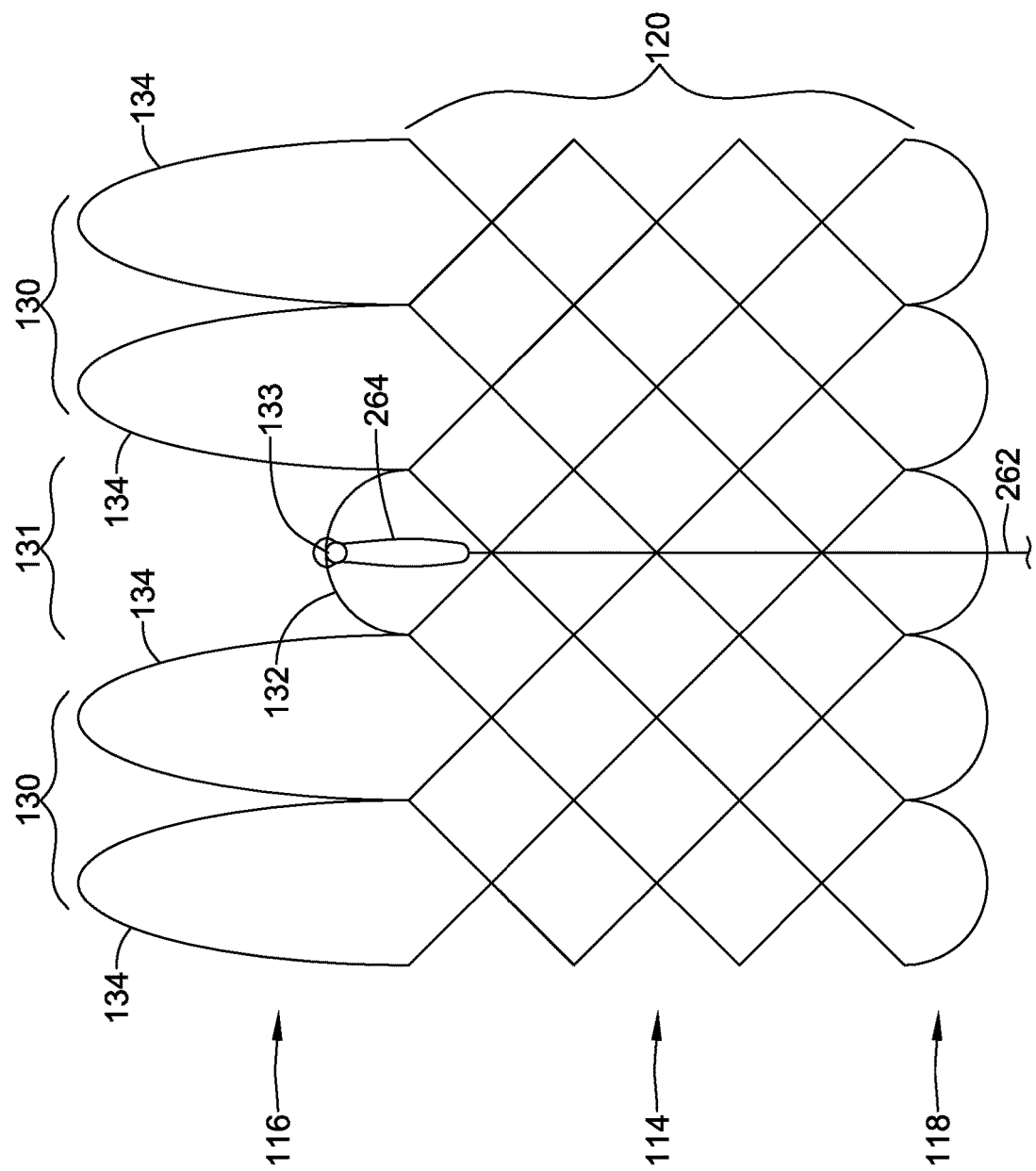
Figure 19:
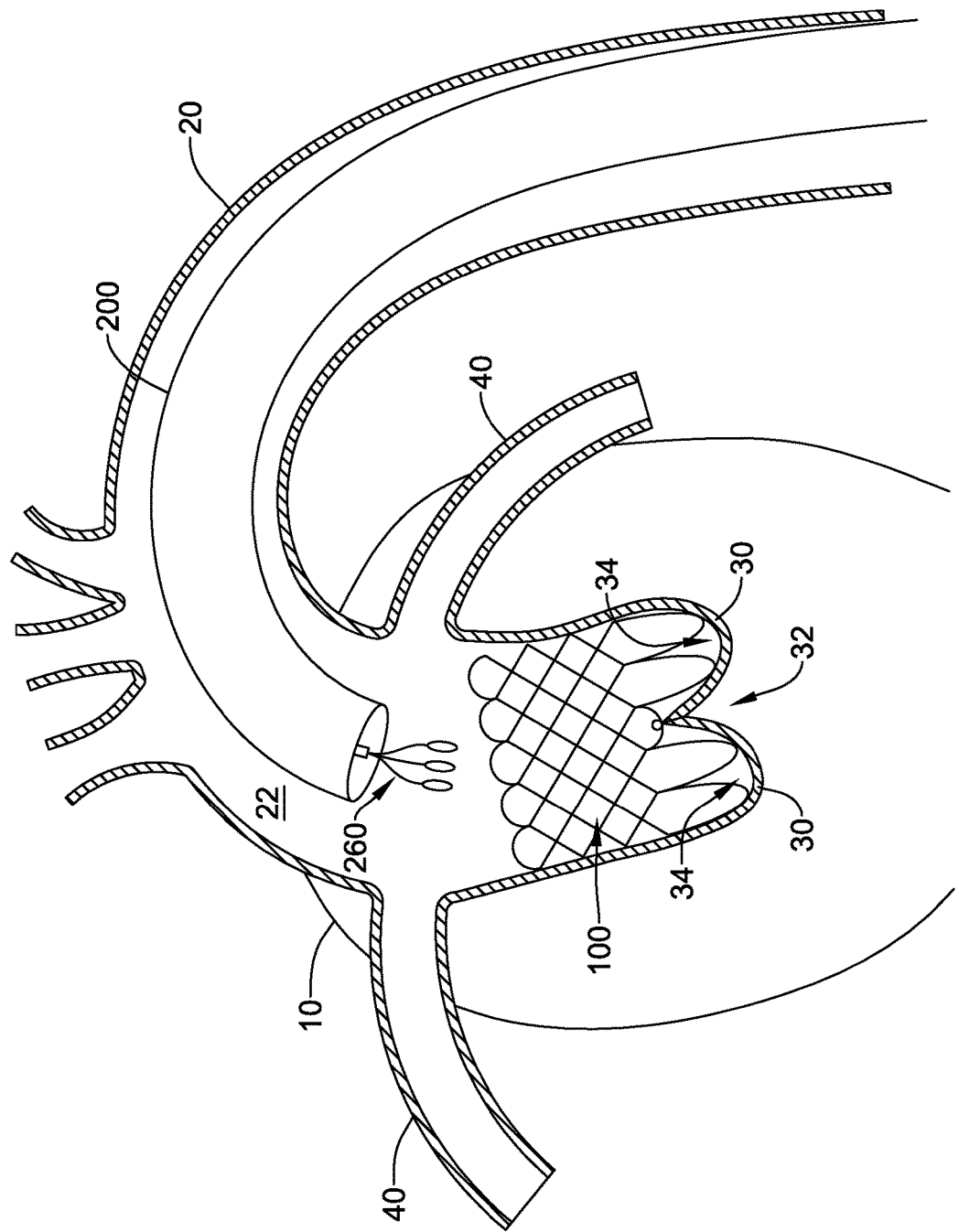

Some embodiments may utilize a mechanical deployment member 250, as seen in FIG. 14 for example. In some embodiments, an anchoring assistance device delivery system may include a delivery sheath 200 having at least one lumen extending longitudinally therethrough and an actuator mechanism 252 disposed at a proximal end of the delivery sheath 200. In some embodiments, an anchoring assistance device delivery system may include an elongate deployment member 250 extending from the actuator mechanism 252 to an anchoring assistance device 100 disposable within a distal portion of the delivery sheath 200, as seen in FIGS. 14-15 for example. In some embodiments, the elongate deployment member 250 may be configured to releasably engage with the deployment rings 133 of the anchoring assistance device 100 such that the elongate deployment member 250 actuates the expandable scaffold 112 from the delivery configuration (as seen in FIG. 16 for example) to the deployed configuration (as seen in FIGS. 17-19 for example) in response to activation of the actuator mechanism 252. In some embodiments, the actuator mechanism 252 may be configured to axially translate the elongate deployment member 250 with respect to the delivery sheath 200 and/or the anchoring assistance device 100.

In some embodiments, the elongate deployment member 250 may include an elongate shaft 256 extending distally from the actuator mechanism 252. In some embodiments, the elongate shaft 256 may be a solid member of fixed length, such as a rod, cylinder, pin, shaft, and the like. In some embodiments, the elongate shaft 256 may be a hollow member of fixed length such as a shaft with one or more lumens extending therethrough, a hypotube, a tubular member, and the like. In some embodiments, the elongate shaft 256 may be a hollow member of variable length with one or more lumens extending therethrough, such as in a telescoping and/or collapsible arrangement. In some embodiments, the elongate shaft 256 may be metallic or polymeric, and flexible or rigid (or semi-rigid), as desired.

In some embodiments, the actuator mechanism 252 may include a handle fixed to a proximal end of the elongate deployment member 250 and/or the elongate shaft 256. In some embodiments, the actuator mechanism 252 may be a proximal end of the elongate deployment member 250 and/or the elongate shaft 256. In some embodiments, the elongate deployment member 250 may include an engagement means 260 disposed at a distal end thereof, the engagement means 260 being configured to releasably engage with the anchoring assistance device 100 and/or the deployment rings 133. In some embodiments, the engagement means 260 may include an inflatable balloon (not shown). In some embodiments, the elongate deployment member 250 and/or the engagement means 260 may include a plurality of deployment loops 264 at a distal end thereof, each deployment loop 264 being configured to releasably engage with one deployment ring 133. In some embodiments, the plurality of deployment loops 264 may be connected to a distal end of the elongate shaft 256 by one or more wires 262 extending therebetween. In some embodiments, one wire 262 may extend from a distal end of the elongate shaft 256 to a proximal end of one deployment loop 264. In other words, each of the plurality of deployment loops 264 may be connected to a distal end of the elongate shaft 256 by a corresponding wire 262. In some embodiments, the one or more wires 262 may extend from the distal end of the elongate shaft 256 through one or more lumens of the elongate shaft 256 to the actuator mechanism 252. In some embodiments, the one or more wires 262 may join together into a single actuator wire extending through the elongate shaft 256 to the actuator mechanism 252. In some embodiments, the one or more wires 262 may be fixedly attached to the distal end of the elongate shaft 256—for example, individually, via the aforementioned single actuator wire, or some combination thereof.

In some embodiments, the actuator mechanism 252 may include an actuator element 254, such as a rotatable wheel, a slide, a lever, a knob, and the like. In at least some embodiments, actuation of the actuator element 254 may proximally retract the elongate shaft 256, the single actuator wire, and/or the one or more wires 262 relative to the actuator mechanism 252. In other words, actuation of the actuator element 254 may translate a distal end of the elongate shaft 256, the single actuator wire, and/or the one or more wires 262 closer to the actuator mechanism 252 (i.e., proximally). In some embodiments, the elongate deployment member 250 may be a substantially fixed element of constant length. In other words, individual elements of the elongate deployment member 250 may be fixed in position relative to each other. Proximal withdrawal of the actuator mechanism 252 may axially translate the elongate deployment member 250 in a proximal direction with respect to the delivery sheath 200 and/or the anchoring assistance device 100.

As may be seen in FIGS. 16-18, each deployment loop 264 may extend at least partially through one deployment ring 133. In some embodiments, each deployment loop 264 may extend completely or almost completely (i.e., greater than 75%, greater than 80%, greater than 90%, etc.) through one deployment ring 133, such as when the expandable scaffold 112 is in the delivery configuration. In some embodiments, proximal withdrawal of the elongate deployment member 250, such as by activation of the actuator mechanism 252, may create an interference between each deployment loop 264 and its corresponding deployment ring 133, such that the expandable scaffold 112 may be actuated from the delivery configuration to the deployed configuration. In at least some embodiments, after achieving the deployed configuration, further proximal withdrawal of the elongate deployment member 250 may pull each deployment loop 264 through its corresponding deployment ring 133 to disengage the elongate deployment member 250 and/or the plurality of deployment loops 264 from the expandable scaffold 112, as seen in FIG. 19 for example. In some embodiments, after achieving the deployed configuration, further proximal withdrawal of the elongate deployment member 250 may pull each deployment loop 264 completely through its corresponding deployment ring 133 to disengage the elongate deployment member 250 and/or the plurality of deployment loops 264 from the expandable scaffold 112.

In some embodiments, the deployment rings 133 may have a maximum inner extent and the plurality of deployment loops 264 may have a maximum outer extent greater than the maximum inner extent of the deployment rings 133 in an undeformed or natural condition. This arrangement may be easily seen in FIG. 16, for example. In some embodiments, the deployment rings 133 may be made or formed from the same material as the expandable scaffold 112, including similar physical characteristics (i.e., size, stiffness, etc.). In some embodiments, the deployment rings 133 may be made or formed from the same material as the expandable scaffold 112, with different physical characteristics (i.e., size, stiffness, etc.) In some embodiments, the deployment rings 133 may be made or formed from a different material having similar physical characteristics to the expandable scaffold 112, or the deployment rings 133 may be made or formed from a different material having different physical characteristics from the expandable scaffold 112.

As mentioned above, an interference is created when the plurality of deployment loops 264 is pulled against and/or through the deployment rings 133, the interference resulting in a pull force required to deform and/or disengage the plurality of deployment loops 264 from the deployment rings 133. A mismatch in the size of the features may create this interference, and in some cases may define the pull force required to deform and/or disengage the plurality of deployment loops 264 from the deployment rings 133. In some embodiments, size of the plurality of deployment loops 264 may affect the pull force required to deform and/or disengage the plurality of deployment loops 264 from the deployment rings 133, wherein larger deployment loops 264 may be easier to deform and pull through the deployment rings 133, thereby reducing the pull force required to deform and/or disengage the plurality of deployment loops 264 from the deployment rings 133. Similarly, larger deployment rings 133 may provide less resistance to deformation and pulling the deployment loops 264 therethrough, thereby reducing the pull force required to deform and/or disengage the plurality of deployment loops 264 from the deployment rings 133. In a similar way, stiffer materials may be less likely to bend, deflect, or deform when an interference is created, and thus the pull force required to deform and/or disengage the plurality of deployment loops 264 from the deployment rings 133 may be higher for such materials. In some embodiments, the plurality of deployment loops 264 may be made or formed from a thinner and/or more flexible material than the deployment rings 133 and/or the expandable scaffold 112, which may reduce the pull force required to deform and/or disengage the plurality of deployment loops 264 from the deployment rings 133.

In some embodiments, the plurality of deployment loops 264 may be formed in a figure-eight configuration. In these embodiments, each "lobe" of the figure-eight may have a maximum outer extent greater than the maximum inner extent of the deployment rings 133. As such, each "lobe" may function in the same or similar manner to the plurality of deployment loops 264 described above. Additionally, the figure-eight configuration may permit the plurality of deployment loops 264 to function as a mechanism of action to both deploy the expandable scaffold 112 (by proximal withdrawal as described above) and to collapse the expandable scaffold 112 back toward the delivery configuration through distal actuation of the elongate deployment member 250 and/or the plurality of deployment loops 264 relative to the expandable scaffold 112 and/or the deployment rings 133.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims. This may include, to the extent that it is appropriate, the use of any of the features of one example embodiment or aspect being used in other embodiments or aspects.

What is claimed is:

1. An anchoring assistance device, comprising:
   an expandable scaffold including a mid-body section defining a central longitudinal axis, the expandable scaffold having a cusp interface section extending axially from a distal end of the mid-body section, and a crown end arrangement extending axially from a proximal end of the mid-body section;
   wherein the expandable scaffold is configured to expand radially outward from a delivery configuration to a deployed configuration;
   wherein the cusp interface section includes a plurality of loop portions arranged at radial intervals about the central longitudinal axis of the expandable scaffold, each loop portion being configured to be positioned adjacent a leaflet of an aortic valve;
   wherein each loop portion includes two cusp loops circumferentially offset from each other,
   wherein each loop portion is circumferentially spaced apart from another loop portion by a region having disposed therein a deployment ring configured to be positioned over and downstream of a commissure of the aortic valve and extending distally a shorter distance from the distal end of the mid-body section than the plurality of loop portions.

2. The anchoring assistance device of claim 1, wherein each region includes a minor loop, each minor loop having the deployment ring coupled thereto.

3. The anchoring assistance device of claim 2, wherein the two cusp loops circumferentially overlap each other at a location distal of the minor loops in the deployed configuration.

4. The anchoring assistance device of claim 2, wherein the two cusp loops are circumferentially spaced apart from each other at a location distal of the minor loops in the deployed configuration.

5. The anchoring assistance device of claim 2, wherein each deployment ring is formed from a coiled loop portion of its minor loop.

6. The anchoring assistance device of claim 2, wherein each deployment ring is integrally formed with its minor loop.

7. The anchoring assistance device of claim 1, wherein each loop portion extends a longer circumferential distance around the central longitudinal axis than each region.

8. The anchoring assistance device of claim 1, wherein the anchoring assistance device includes an equal number of loop portions and regions.

9. An anchoring assistance device delivery system, comprising:
a delivery sheath having at least one lumen extending longitudinally therethrough and an actuator mechanism disposed at a proximal end of the delivery sheath;
an elongate deployment member extending from the actuator mechanism to an anchoring assistance device disposable within a distal portion of the delivery sheath, the anchoring assistance device comprising:
an expandable scaffold including a mid-body section defining a central longitudinal axis, the expandable scaffold having a cusp interface section extending axially from a distal end of the mid-body section, and a crown end arrangement extending axially from a proximal end of the mid-body section;
wherein the expandable scaffold is configured to expand radially outward from a delivery configuration to a deployed configuration;
wherein the cusp interface section includes a plurality of loop portions arranged at radial intervals about the central longitudinal axis of the expandable scaffold, each loop portion being configured to be positioned adjacent a leaflet of an aortic valve;
wherein each loop portion is circumferentially spaced apart from another loop portion by a region having disposed therein a deployment ring configured to be positioned over and downstream of a commissure of the aortic valve and extending distally a shorter distance from the distal end of the mid-body section than the plurality of loop portions;
wherein the elongate deployment member is configured to releasably engage with each deployment ring such that the elongate deployment member actuates the expandable scaffold from the delivery configuration to the deployed configuration in response to activation of the actuator mechanism,
wherein the elongate deployment member includes a plurality of deployment loops at a distal end thereof, each deployment loop being configured to releasably engage with one deployment ring,
wherein each deployment loop extends at least partially through one deployment ring,
wherein proximal withdrawal of the elongate deployment member creates an interference between each deployment loop and its corresponding deployment ring such that the expandable scaffold is actuated from the delivery configuration to the deployed configuration.

10. The anchoring assistance device delivery system of claim 9, wherein the actuator mechanism is configured to axially translate the elongate deployment member with respect to the delivery sheath.

11. The anchoring assistance device delivery system of claim 9, wherein after achieving the deployed configuration, further proximal withdrawal of the elongate deployment member pulls each deployment loop through its corresponding deployment ring to disengage the elongate deployment member from the expandable scaffold.

12. A medical implant system, comprising:
a delivery sheath having at least one lumen extending longitudinally therethrough and an actuator mechanism disposed at a proximal end of the delivery sheath;
an anchoring assistance device comprising an expandable scaffold including a mid-body section defining a central longitudinal axis, the expandable scaffold having a cusp interface section extending axially from a distal end of the mid-body section, and a crown end arrangement extending axially from a proximal end of the mid-body section; and
a replacement heart valve implant;
wherein the expandable scaffold is configured to expand radially outward from a delivery configuration to a deployed configuration;
wherein the cusp interface section includes a plurality of loop portions arranged at radial intervals about the central longitudinal axis of the expandable scaffold, each loop portion being configured to be positioned adjacent a leaflet of an aortic valve;
wherein each loop portion is circumferentially spaced apart from another loop portion by a region having disposed therein a deployment ring configured to be positioned over and downstream of a commissure of the aortic valve and extending distally a shorter distance from the distal end of the mid-body section than the plurality of loop portions;
wherein an elongate deployment member extends from the actuator mechanism to the anchoring assistance device, the anchoring assistance device being disposable within a distal portion of the delivery sheath;
wherein the elongate deployment member is configured to releasably engage with each deployment ring to actuate the expandable scaffold from the delivery configuration to the deployed configuration;
wherein the replacement heart valve implant is configured to be at least partially disposed within the expandable scaffold in the deployed configuration,
wherein the elongate deployment member includes a plurality of deployment loops at a distal end thereof, each deployment loop being configured to releasably engage with one deployment ring;
wherein proximal withdrawal of the elongate deployment member creates an interference between each deployment loop and its corresponding deployment ring such that the expandable scaffold is actuated from the delivery configuration to the deployed configuration.

13. The medical implant system of claim 12, wherein the replacement heart valve implant includes a transcatheter aortic valve implantation (TAVI) device or a transcatheter aortic valve replacement (TAVR) device.

14. The medical implant system of claim 12, wherein the replacement heart valve implant includes an anchor member expandable from a collapsed configuration to an installed configuration, the anchor member being configured to radially engage the expandable scaffold in the installed configuration.

15. The medical implant system of claim 14, wherein the anchoring assistance device prevents migration of the replacement heart valve implant when the anchor member is radially engaged with the expandable scaffold.

* * * * *